(12) United States Patent
Maher et al.

(10) Patent No.: US 10,583,224 B2
(45) Date of Patent: Mar. 10, 2020

(54) MULTI-COMPONENT NON-BIODEGRADABLE IMPLANT, A METHOD OF MAKING AND A METHOD OF IMPLANTATION

(71) Applicant: NEW YORK SOCIETY FOR THE RUPTURED AND CRIPPLED MAINTAINING THE HOSPITAL FOR SPECIAL SURGERY, New York, NY (US)

(72) Inventors: Suzanne A. Maher, Highland Lakes, NJ (US); Tony Chen, New Brunswick, NJ (US); Joseph D. Lipman, New York, NY (US); Peter Torzilli, Ridgefield, CT (US); Russell Warren, Greenwich, CT (US)

(73) Assignee: NEW YORK SOCIETY FOR THE RUPTURED AND CRIPPLED MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 314 days.

(21) Appl. No.: 15/370,832

(22) Filed: Dec. 6, 2016

(65) Prior Publication Data

US 2017/0209624 A1     Jul. 27, 2017

Related U.S. Application Data

(63) Continuation of application No. 14/261,821, filed on Apr. 25, 2014, now Pat. No. 9,545,310.

(Continued)

(51) Int. Cl.
*A61F 2/30*     (2006.01)
*A61L 27/56*    (2006.01)
(Continued)

(52) U.S. Cl.
CPC .............. *A61L 27/56* (2013.01); *A61F 2/0811* (2013.01); *A61F 2/28* (2013.01); *A61F 2/3094* (2013.01);
(Continued)

(58) Field of Classification Search
CPC ......... A61L 27/52; A61L 27/56; B29C 70/70; A61F 2/3094
See application file for complete search history.

(56) References Cited

U.S. PATENT DOCUMENTS 5,002,580 A    3/1991  Noble et al.
5,282,861 A    2/1994  Kaplan
(Continued)

FOREIGN PATENT DOCUMENTS

JP    07-055588    3/1995
JP    08-066373    3/1996
(Continued)

OTHER PUBLICATIONS

Peppas et al., "Structure and Morphology of Freeze/Thawed PVA Hydrogels", Macromolecules 2000 33 (7), p. 2472-2479 (Year: 2000).*

(Continued)

*Primary Examiner* — Galen H Hauth
(74) *Attorney, Agent, or Firm* — Leason Ellis LLP

(57) ABSTRACT

An implant comprising at least three components, namely, a solid hydrogel, a porous hydrogel adjacent to or surrounding the solid hydrogel (together considered "the hydrogel"), and a porous rigid base. The solid hydrogel and porous rigid base carry joint load, and the porous hydrogel layer and the porous rigid base allow for cellular migration into and around the implant. The invention is also a novel method of manufacturing the implant, a novel method of implanting the implant, and a method of treating, repairing or replacing (Continued)

biological tissue, more preferably musculoskeletal tissue, with the implant.

11 Claims, 16 Drawing Sheets

Related U.S. Application Data

(60) Provisional application No. 61/816,209, filed on Apr. 26, 2013.

(51) Int. Cl.

| | | |
|---|---|---|
| *B29C 70/70* | (2006.01) | |
| *A61F 2/38* | (2006.01) | |
| *A61F 2/28* | (2006.01) | |
| *A61F 2/44* | (2006.01) | |
| *A61F 2/08* | (2006.01) | |
| *A61L 27/16* | (2006.01) | |
| *A61L 27/18* | (2006.01) | |
| *A61L 27/52* | (2006.01) | |
| *A61L 27/54* | (2006.01) | |
| *B29C 71/02* | (2006.01) | |
| *A61B 17/16* | (2006.01) | |
| *B29K 29/00* | (2006.01) | |
| *B29K 105/00* | (2006.01) | |
| *B29L 31/00* | (2006.01) | |

(52) U.S. Cl.
CPC ........ *A61F 2/30756* (2013.01); *A61F 2/3872* (2013.01); *A61F 2/442* (2013.01); *A61L 27/16* (2013.01); *A61L 27/18* (2013.01); *A61L 27/52* (2013.01); *A61L 27/54* (2013.01); *B29C 70/70* (2013.01); *B29C 71/02* (2013.01); *A61B 17/1675* (2013.01); *A61F 2002/087* (2013.01); *A61F 2002/0817* (2013.01); *A61F 2002/0858* (2013.01); *A61F 2002/0888* (2013.01); *A61F 2002/30075* (2013.01); *A61F 2210/0061* (2013.01); *A61L 2430/02* (2013.01); *A61L 2430/06* (2013.01); *A61L 2430/10* (2013.01); *A61L 2430/24* (2013.01); *A61L 2430/38* (2013.01); *B29K 2029/04* (2013.01); *B29K 2105/0061* (2013.01); *B29K 2995/006* (2013.01); *B29L 2031/7532* (2013.01)

(56) References Cited

U.S. PATENT DOCUMENTS

| | | | |
|---|---|---|---|
| 6,132,465 | A | 10/2000 | Ray et al. |
| 6,592,588 | B1 | 7/2003 | Bobic et al. |
| 2004/0262809 | A1 | 12/2004 | Smith et al. |
| 2005/0273100 | A1 | 12/2005 | Taylor |
| 2006/0095077 | A1* | 5/2006 | Tronnes ............... A61N 1/375 607/2 |
| 2006/0178748 | A1 | 8/2006 | Dinger, III et al. |
| 2007/0225823 | A1* | 9/2007 | Hawkins ............... A61L 27/28 623/23.51 |
| 2009/0017096 | A1* | 1/2009 | Lowman ............... A61F 2/28 424/426 |
| 2010/0023130 | A1* | 1/2010 | Henry ................... A61L 27/48 623/17.18 |
| 2010/0032090 | A1 | 2/2010 | Myung et al. |
| 2010/0268261 | A1 | 10/2010 | Nycz et al. |
| 2010/0268337 | A1 | 10/2010 | Gordon et al. |
| 2011/0098966 | A1 | 4/2011 | Suzuki |
| 2012/0041563 | A1 | 2/2012 | Chudik |
| 2012/0178836 | A1 | 7/2012 | Maher et al. |

FOREIGN PATENT DOCUMENTS

| | | |
|---|---|---|
| JP | 2005-003596 | 1/2005 |
| JP | 2010-14501 | 1/2010 |
| WO | WO 2010/014446 | 2/2010 |
| WO | WO-2011/107807 | 9/2011 |
| WO | WO-2012/065068 | 5/2012 |

OTHER PUBLICATIONS

Bekkers, J. E., et al. (Nov. 24, 2009). "Treatment selection in articular cartilage lesions of the knee: a systematic review." Am J Sports Med 37 Suppl 1: 148S-155S.

Choi, K., et al. (Apr. 20, 1990) "The elastic moduli of human subchondral, trabecular, and cortical bone tissue and the size-dependency of cortical bone modulus." J Biomech 23(11):1103-13.

Cole, B. J. and S. J. Lee (Dec. 2003). "Complex knee reconstruction: articular cartilage treatment options." Arthroscopy 19 Suppl 1: 1-10.

Deneweth, J.M., et al. (2013) "Heterogeneity of tibial plateau cartilage in response to a physiological compressive strain rate." J Orthop Res 31(3):370-5. Accepted Aug. 16, 2012.

Magnussen, R. A., et al. (Jan. 12, 2008). "Treatment of focal articular cartilage defects in the knee: a systematic review." Clin Orthop Relat Res 466(4): 952-962.

Mauck, R. L., et al. (Aug. 14, 2002). "Influence of seeding density and dynamic deformational loading on the developing structure/function relationships of chondrocyte-seeded agarose hydrogels." Ann Biomed Eng 30(8): 1046-1056.

Ng, K.W., et al. (May 11, 2012) "A novel macroporous polyvinyl alcohol scaffold promotes chondrocyte migration and interface formation in an in vitro cartilage defect model." Tissue Eng Part A 18(11-12): 1273-81.

Radin, E.L., et al. (Apr. 1970) "A comparison of the dynamic force transmitting properties of subchondral bone and articular cartilage." J Bone Joint Surg Am 52(3):444-56.

Shelbourne, K. D., et al. (Apr. 2003). "Outcome of untreated traumatic articular cartilage defects of the knee: a natural history study." J Bone Joint Surg Am 85-A Suppl 2: 8-16.

\* cited by examiner

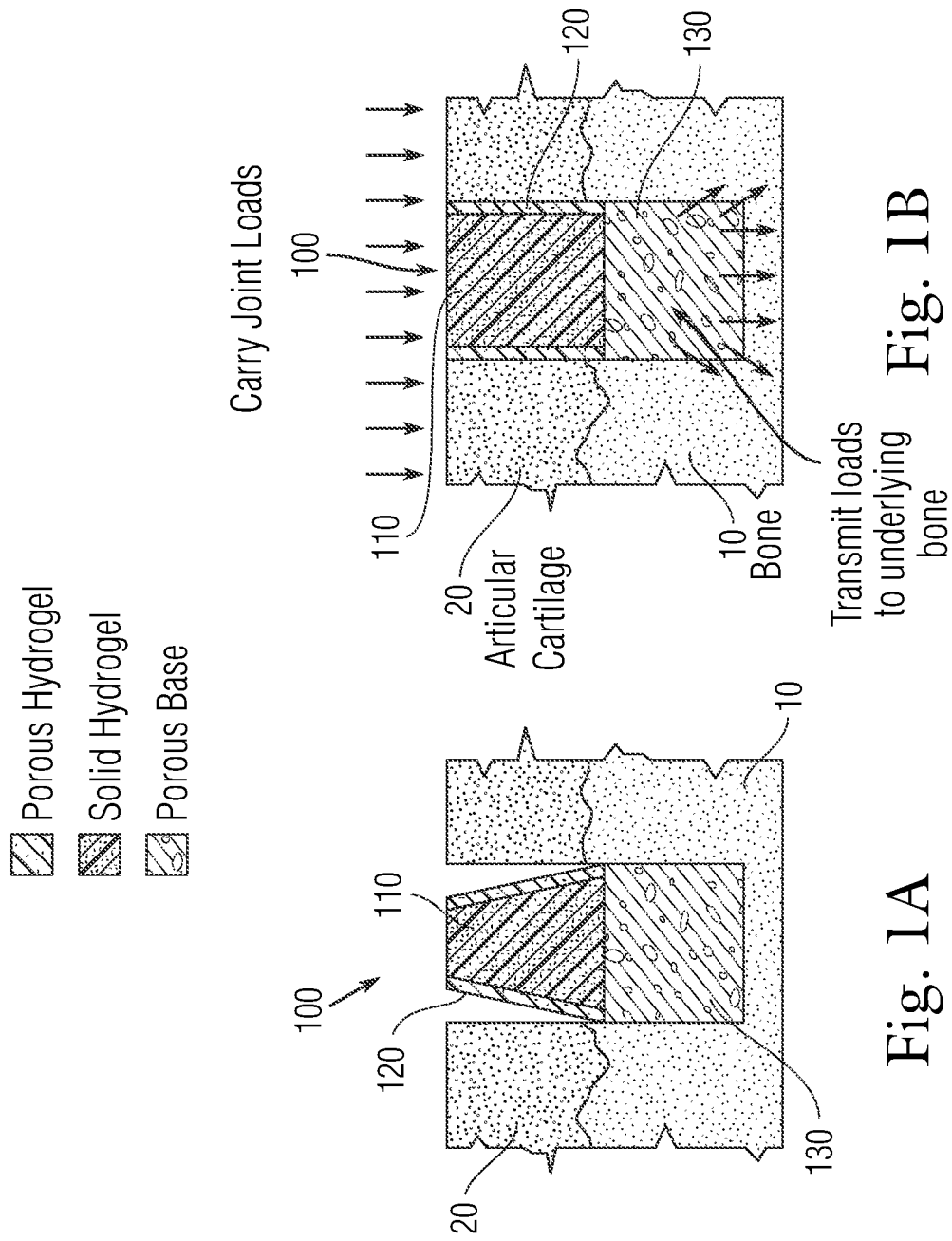

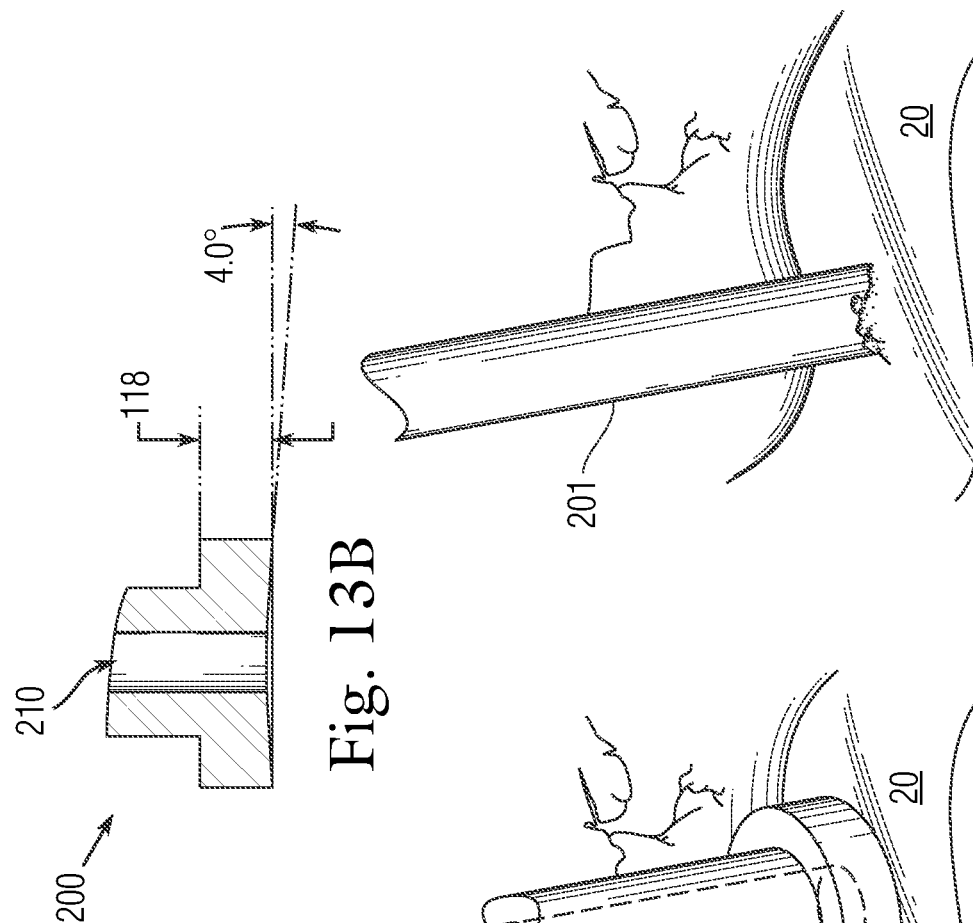
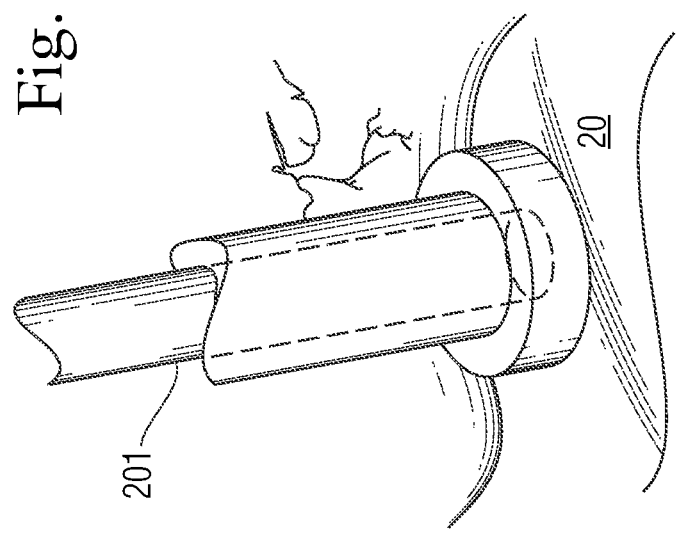
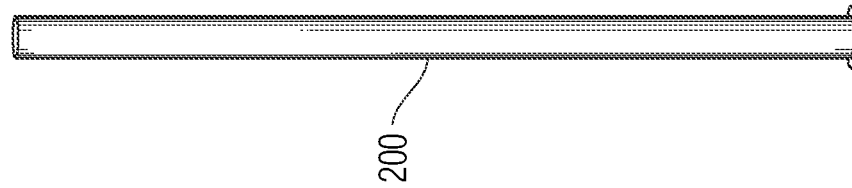

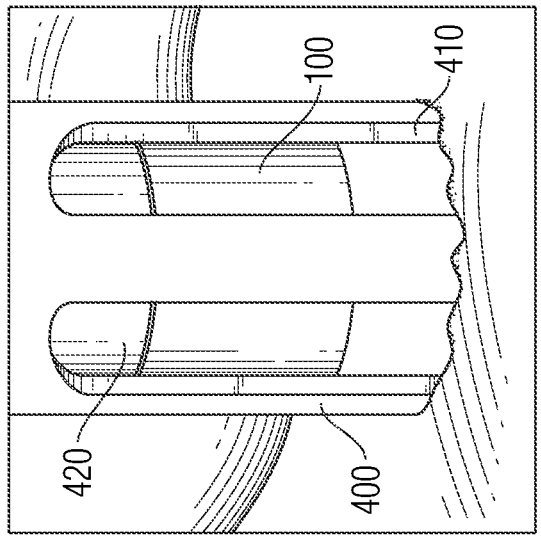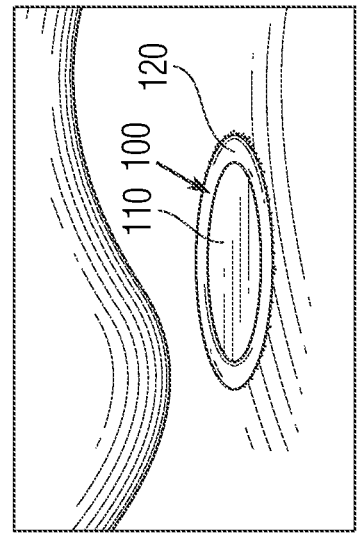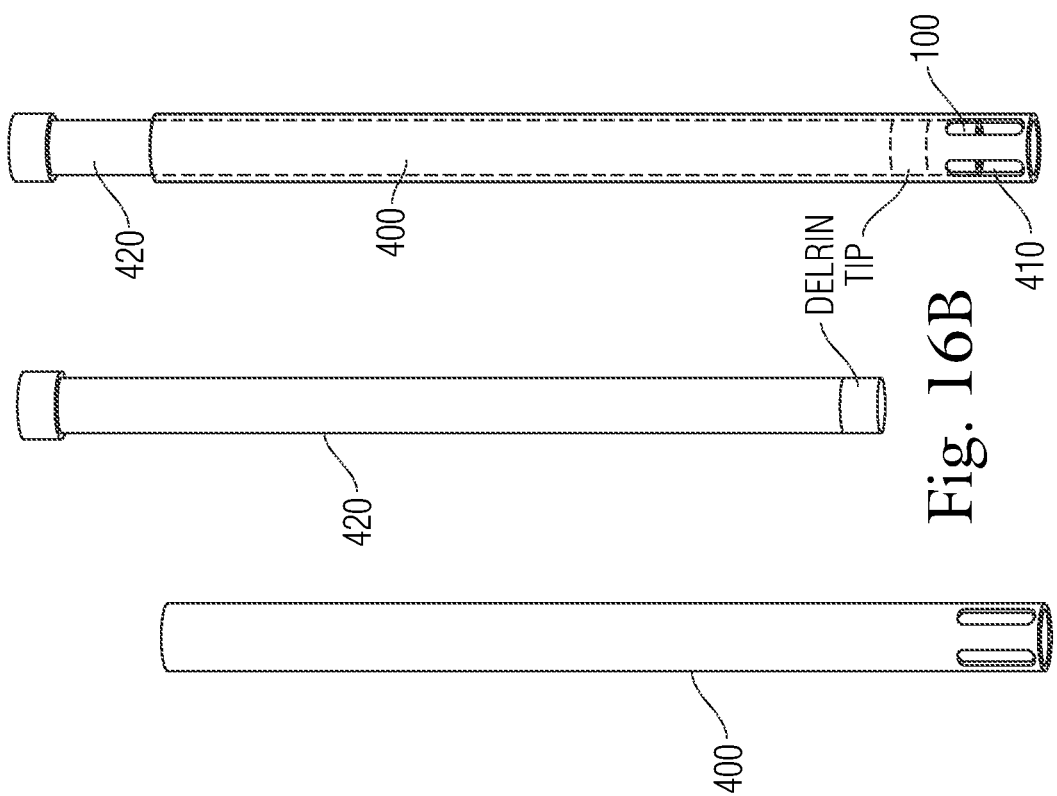

MULTI-COMPONENT NON-BIODEGRADABLE IMPLANT, A METHOD OF MAKING AND A METHOD OF IMPLANTATION

CROSS-REFERENCE TO RELATED PATENT APPLICATIONS

The present application is a continuation of U.S. patent application Ser. No. 14/261,821, filed Apr. 25, 2014, which claims priority to U.S. patent application Ser. No. 61/816,209, filed Apr. 26, 2013, each of which is hereby incorporated by reference as if expressly set forth in their respective entirety herein.

FIELD OF THE INVENTION

The present invention relates to a multi-component implant comprising a solid hydrogel, a porous hydrogel, and a porous rigid base suitable for implantation into a mammal, to treat, repair or replace defects and/or injury to musculoskeletal tissue, a method of manufacturing the multi-component implant, and a method of implantation.

BACKGROUND OF THE INVENTION

Articular cartilage defects in joints are a significant source of pain, have a limited ability to heal, and can lead to the development of osteoarthritis (Buckwalter and Mankin, 1998; Shelbourne et al., 2003). Surgical options for symptomatic cartilage defects include palliative, reparative, and restorative methods (Cole and Lee, 2003). However the treatment algorithm and surgical indications for each of these procedures continues to evolve (Magnussen et al., 2008; Bekkers et al., 2009). Alternative treatments have been developed using biodegradable implants intended to encourage the formation of articular cartilage within the defect site. However, these implants have mechanical properties that are continually changing and often inferior to that of the native tissue during the regeneration process (Mauck et al., 2002). Furthermore, these implants rely on a controlled and robust cellular response in order to recreate an organized tissue that looks and mechanically functions like the native articular cartilage, a goal that has thus far proven elusive in the biological environment of the defective joint.

Another method to treat this clinical problem is to use well characterized, non-biodegradable implants capable of resisting in vivo mechanical loads immediately after implantation and for the duration of the regeneration process. Non-degradable constructs should ideally: (i) integrate with adjacent tissue; (ii) transmit loads much in the way of the native tissue that the implant is intended to replace; (iii) transfer load to the underlying bone (to avoid bony resorption); (iv) resist wear; (v) not cause abrasion to opposing cartilage surfaces; and (vi) allow for easy implantation and fixation to the surrounding tissues. However, to date, such an implant has not been developed that fulfills all of these criteria.

SUMMARY OF THE INVENTION

The present invention overcomes the problems in the art by providing a novel implant for treating, repairing, and/or replacing a defect and/or injury in biological tissue or the biological tissue as a whole, more specifically musculoskeletal tissue, that meets the six requirements set forth above. It also provides a method to manufacture the novel implant, a method to treat, repair and/or replace a defect and/or injury in biological tissue with the implant, and a method to implant or insert the implant.

Thus, one embodiment of the present invention is an implant comprising at least three components: a solid hydrogel or polymer, a porous hydrogel or polymer that can surround the solid hydrogel or polymer (together considered "the hydrogel", "hydrogel layer" or "hydrogel portion"); and a porous rigid base. Other embodiments of the implant can comprise of multiple solid hydrogel or polymer sections within the porous hydrogel or polymer, or layers of solid hydrogel or polymer and porous hydrogel or polymer. In every embodiment of the current invention, the porous hydrogel or polymer is adjacent to the solid hydrogel or polymer. The hydrogel portion of the implant can be integrated with one, or two or more porous rigid bases. The solid hydrogel(s) and porous rigid base(s) resist joint load, and the porous hydrogel(s) and the porous rigid base(s) allow for cellular migration into and around the implant.

The implant of the present invention can also comprise an interface that maximizes integration between the two very different layers—the hydrogel and the porous rigid base. This interface can comprise a hydrogel or polymer layer of high or low viscosity that interdigitates into the micro- and macropores and other features of the porous rigid base. These geometric features such as micro- and macropores, as well as holes, tapers, and steps are either part of, or added to the porous rigid base, and facilitate the integration.

The implant of the present invention also has features allowing for ease of implantation. One such feature is that the hydrogel portion of the implant can be dehydrated prior to implantation such that the hydrogel decreases in size and/or changes shape, and upon implantation and rehydration, the hydrogel increases in size and/or regains its shape. Another feature of the hydrogel portion of the implant is that upon dehydration, the hydrogel stiffens such that the implant can be inserted into the defect by pressing the hydrogel without the hydrogel changing shape.

Another feature of the implant that facilitates implantation is that the porous rigid base is tapered at the bottom to provide self-alignment of the implant with the defect or injury.

The implant can also comprise other agents that facilitate migration, integration, regeneration, proliferation, and growth of cells into and around the implant or patch composition, and/or the injury or defect, and/or promote healing of the injury or defect, and/or are chondrogenic and osteogenic, i.e., build, grow and produce cartilage and bone, respectively.

These agents, include but are not limited to, cytokines, chemokines, chemoattractants, anti-microbials, anti-virals, anti-inflammatories, pro-inflammatories, bone or cartilage regenerator molecules, cells, blood components (e.g., whole blood and platelets), and combinations thereof.

Agents that increase strength and facilitate attachment can also be included in the implant.

A further embodiment of the present invention is a method of manufacturing or producing an implant suitable for implantation into a mammal for the treatment, repair or replacement of defects or injury in biological tissue, more specifically, musculoskeletal tissue, comprising:

a. creating a porous rigid base with macropores and other features in the surface;

b. adding a hydrogel or polymer of low or high viscosity to the macropores and other features and the surface of the porous rigid base, such that the macropores and features are filled and the surface covered, to create a porous rigid base-polymer construct;

c. placing a hydrogel on the porous rigid base-polymer construct to create the implant; and d. freezing and thawing the implant;

wherein the freeze/thaw process is performed 1 to 5 times.

In a further embodiment, the hydrogel in step (c) comprises one or more solid hydrogel(s) and porous hydrogel layer(s) and can be made by a method comprising the steps:

a. soaking a degradable polymer sponge in deionized water for a period of about 1 hour to 5 days;

b. centrifuging the sponge during the soaking;

c. substituting the water with a non-biodegradable polymer in steps of increasing concentration up to a desired final concentration;

d. cross-linking the non-biodegradable polymer;

e. removing a center section from the sponge after performing steps a.-d;

f. adding additional non-biodegradable polymer to the center section; and g. performing additional cross-linking processes.

The cross-linking process can include but is not limited to methods such as freeze/thaw cycles. A preferred freeze/thaw cycle comprises freezing the sponge to about −20° C. for about 4 to 24 hours and subsequently thawing the sponge at about 25° C. for about 4 to 12 hours, and is performed 1 to 8 times. The method of manufacture can further comprise digesting away the degradable polymer in the implant and/or dehydrating the implant prior to implantation. Enzymatic digestion is preferred.

The present invention also comprises a method of implanting or inserting the implant into a mammal for the treatment, repair or replacement of a defect or injury in musculoskeletal tissue, comprising:

a. dehydrating the implant so that the solid hydrogel and porous hydrogel of the implant changes shape and is smaller than the size of defect or injury;

b. placing a wire perpendicular to the surface of the musculoskeletal tissue surrounding the defect or injury;

c. cutting the edges of the musculoskeletal tissue surrounding the defect or injury to create a clean circular edge around the defect or injury and to measure the thickness of the surrounding musculoskeletal tissue;

d. drilling the defect or injury;

e. measuring the final depth of the defect or injury;

f. choosing an implant size based upon the final depth of the defect or injury and/or the depth of the musculoskeletal tissue, and optionally partially re-hydrating the implant using a supplemental agent;

g. inserting the implant into a delivery tube and inserting a rod into the delivery tube;

h. placing the delivery tube over the defect or injury; and i. inserting the implant into the defect or injury by using the rod in the delivery tube.

The implant will then rehydrate with surrounding bodily fluids, and the hydrogel portion of the implant will expand to fill the defect. Using this method can insure that the implant is inserted contiguous or proud to the adjacent tissue.

Yet a further embodiment of the present invention is a novel method to treat, repair and/or replace defects and/or injuries to biological tissue, more specifically musculoskeletal tissue, by implanting the novel implant into a subject in need thereof.

A further embodiment of the present invention is a kit comprising the implant, various tools for implantation, supplemental agents, and instructions.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

FIG. 1A is a schematic illustrating the device after implantation into a defect, where the hydrogel is dehydrated. FIG. 1B is a schematic picture of the implant used to treat, repair or replace cartilage and bone defects or injury, i.e., osteochondral defect, which includes a solid hydrogel to resist load, a porous hydrogel layer for cartilage integration and a porous rigid base for tissue integration and transmission of loads to the underlying bone.

FIG. 7A is the entire base and FIG. 7B is close-up showing the location of the taper.

FIG. 10A shows a centering jig used in present invention to maintain consistent positioning of the center cored region of the hydrogel. FIG. 10B shows the use of a concentric cutting die.

FIG. 13A is a side view of a K-wire alignment tool. FIG. 13B shows that the alignment tool has a surface curvature that matches that of the cartilage surface and FIG. 13B shows that the tool has a cannula in which a K-wire can be passed through and placed perpendicular to the articular cartilage surface as shown in FIGS. 13C and 13D.

FIG. 14A shows the cartilage scoring instrument which is cannulated to fit over the k-wire.

FIG. 15A shows a cannulated 9 mm half-moon diameter reamer is placed over the K-wire on the surface of the cartilage and material is removed. FIG. 15B illustrates that the K-wire is then removed and FIG. 15C shows that material remaining in the defect is cleared. FIG. 15D shows a 9 mm diameter measuring instrument used to more accurately measure the depth of the defect.

FIGS. 16A-E show a tool for implanting the device. FIG. 16A is a view of an implant delivery tube. FIG. 16B shows an insertion rod and FIG. 16C shows the delivery tube with the insertion rod placed inside of the delivery tube. FIG. 16D is a view of the delivery system disposing the implant into the defect and FIG. 16E is a view of the implant after being placed into the defect.

DETAILED DESCRIPTION OF INVENTION

Definitions

Figure 1C:
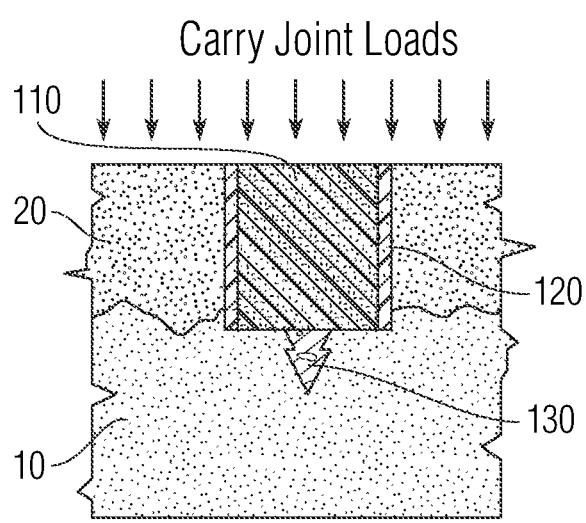
FIG. 1C is a schematic illustrating the use of the implant to treat, repair or replace cartilage defects or injury using a smaller porous rigid base.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The terms "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The terms "implant", "device", and "construct", are used interchangeably throughout this application and means any material inserted or grafted into the body that maintains support and tissue contour.

The term "porous" as used in the application means having pores, which are defined as a minute opening.

The term "micropores" as used in the application means pores with a diameter of less than about 1 mm, and the term "microporous" means having micropores or pores with a diameter less than about 1 mm.

The term "macropores" as used in the application means pores with a diameter greater than about 1 mm, and the term "macroporous" means having macropores or pores with a diameter greater than about 1 mm.

The term "interconnected" as used in the application means having internal connections or continuity between parts or elements.

The term "rigid" as used in the application means a porous material that has an elastic modulus that is about at least 20 times greater than the hydrogel or polymer it is interfaced with. This minimum fold difference was determined from the previously measured elastic moduli for cartilage (ranges from 7.01 MPa to 40 MPa) (Deneweth et al., 2012; Radin et al., 1970) and bone (785 to 1,115 MPa) (Radin et al., 1970; Choi et al., 1990). In some embodiments, the porous rigid base can have an elastic modulus greater than bone.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications The term "in need thereof" would be a subject known or suspected of having an injury to or defect in biological tissue including, but not limited to musculoskeletal tissues, arteries and blood vessels, and organs. Musculoskeletal tissue includes but is not limited to, cartilage, bone, tendon, ligaments, meniscus, temporomandibular joint, and the discs of the spine but can be adapted to any tissue that is comprised of two tissue types, e.g., bone and cartilage. The current invention is particularly suited for humans with osteochondral defects or injuries.

The terms "treat", "treatment", and the like refer to a means to slow down, relieve, ameliorate or alleviate at least one of the symptoms of the defect or injury or reverse the defect or injury after its onset.

The term "repair" and the like refer to any correction, reinforcement, reconditioning, remedy, making up for, making sound, renewal, mending, patching, or the like that restores function. Accordingly, the term "repair" can also mean to correct, to reinforce, to recondition, to remedy, to make up for, to make sound, to renew, to mend, to patch or to otherwise restore function.

The term "replace", "replacement", and the like refer to a means to substitute or take the place of defective or injured tissue.

The term "defect" and the like refer to a flaw or a physical problem in a structure, or system, especially one that prevents it from functioning correctly, or a medical abnormality. Defects can include, but are not limited to, wounds, ulcers, burns, natural defects, such as birth defects, and any other defects of biological tissue, including skin, bone, cartilage, muscle, tendon, ligament, meniscus, temporomandibular joint, arteries and blood vessels, and organs.

The term "injury" and the like refer to wound or trauma; harm or hurt; usually applied to damage inflicted on the body by an external force.

The term "proud" as used in the application means less than or equal to about 1 mm above the adjacent tissue, with about 0.5 mm above the adjacent tissue being preferred, and about 0.3 mm above the adjacent tissue being most preferred.

The term "polymer" means a large molecule composed of repeating structural units often connected by covalent chemical bonds. Polymers can be natural or synthetic. "Biodegradable polymers" are those that can be degraded by living organisms or molecules produced by living organisms such as enzymes and other proteins, and "non-biodegradable polymers" cannot be degraded by such enzymes or proteins. The non-biodegradable polymer as used herein means any polymer that has mechanical properties that can be controlled separately by varying the polymer concentration and/or the method of polymerization such as freeze/thawing.

"Degradable polymers" include biodegradable polymers as well as polymers that can be degraded using other methods such as but not limited to acid/base erosion, solubilization and melting.

"Non-degradable polymers" cannot be degraded by anything.

The term "hydrogel" means a degradable or non-degradable natural or synthetic polymer network which is hydrophilic and can absorb a high amount of water. The hydrogel as used herein means any hydrogel that has mechanical properties that can be controlled separately by varying the polymer and water concentrations and/or the method of gelation such as freeze/thawing.

The terms "polymerization" and "gelation" and the like refer to a means to polymerize, solidify, gel, interconnect, integrate, and the like to form polymer or hydrogel three-dimensional networks.

The term "biocompatible" as used in the application means capable of coexistence with tissues or organisms without causing harm.

The term "extracellular matrix" as used in the application means the substance of a tissue outside and between cells.

The term "moiety" as used in the application means part of a composition that exhibits a particular set of chemical and pharmacologic characteristics. "Biological moieties" are those which derive from living organisms or through protein engineering. "Chemical moieties" do not derive from living organisms.

The term "agent" as used herein means a substance that produces or is capable of producing an effect and would include, but is not limited to, chemicals, pharmaceuticals, biologics, small organic molecules, cells, blood products, antibodies, nucleic acids, peptides, and proteins.

The term "supplemental agent" as used herein would mean an agent that is added to the implant to impart beneficial properties to the implant.

The Multi-Component Implant

A novel multi-component implant 100 of one exemplary embodiment of the present invention comprises a solid hydrogel 110 to resist load, a porous hydrogel layer 120 to enable cellular infiltration and implant-tissue integration, and a porous rigid base 130 to which the solid and porous hydrogels 110, 120 are both attached. As set forth below, in certain embodiments, only the solid hydrogel 110 is attached to the porous rigid case 130. As shown in the figures, the porous hydrogel layer 120 is disposed over at least a portion of the solid hydrogel 110 and therefore, in some embodiments, the layer 120 can be thought of as surrounding at least a portion of the solid hydrogel 110. It will be appreciated that the illustrated layer 120 is not applied to all of the surfaces of solid hydrogel 110 in at least some embodiments and in particular, when the solid hydrogel 110 is formed to have a top surface, a bottom surface and a side surface, the layer 120 can be applied so as to be disposed about the side of the solid hydrogel 110, thereby leaving the top and bottom uncovered as shown in FIGS. 1A and 1B. However, it will be understood that the porous layer 120 can be applied to more than one surface (e.g., across the top as well) of the solid hydrogel 110. In some embodiments, the solid hydrogel 110 can resemble a core and the layer 120 can have an annular shape. However, these are merely exemplary shapes and not limiting of the present invention.

There are many advantages to the implant 100 of the present invention. Integration between the implant 100, and cartilage 20 and bone tissue 10 simultaneously occur. Loads acting on the hydrogel surface are transmitted through the hydrogel solid 110 to the porous rigid base 130 and underlying bone 10. In addition, the implant 100 or construct is provided to the surgeon as a dehydrated entity, allowing it to be more easily implanted into the defect or injury site at the time of surgery. Once the implant 100 is in place, the hydrogel portion of the implant rehydrates with surrounding joint fluid and swells to fill the site of implantation.

A schematic of the implant design 100 is illustrated in FIG. 1A. Note the shape of the dehydrated hydrogel/polymer 110, 120 upon implantation. Hydration of the device 100 with joint fluids will cause an expansion of the hydrogel/polymer 110, 120 to fill the defect as illustrated in FIG. 1B.

FIG. 1B shows device 100 for use in an osteochondral defect, where a larger portion of the bone 10 would need to be repaired or replaced with the porous rigid base 130. The schematic also illustrates the functional requirements of the device 100 for the defect: the solid hydrogel/polymer 110 to carry load; the porous hydrogel/polymer layer 120 for cartilage integration; and the porous rigid base 130 for bony integration and transmission of loads to the underlying bone 10.

FIG. 1C shows a schematic of a device 100 for use in an osteochondral defect where less or no bone needs to be repaired or replaced. The porous rigid base 130 in this embodiment is smaller, as compared to the hydrogel/polymer 110, 120, and acts as an anchor to fix the implant into the defect. In this embodiment, the rigid base 130 does not interface with the porous hydrogel 120.

Figure 1D:
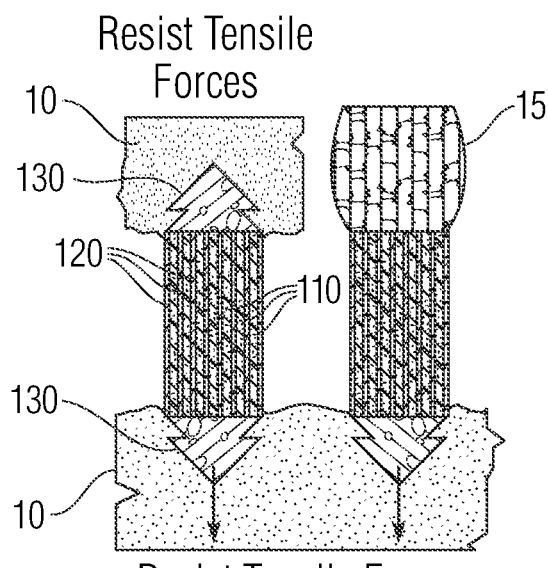
FIG. 1D is a schematic that illustrates the use of the implant to treat, repair, or replace ligaments (left) and tendons (right).

FIG. 1D is a schematic of an embodiment of the implant 100 for use in to repair or replace a ligament (left figure showing attaching bone 10 to bone 10) and tendon (right figure showing attaching bone 10 to muscle 15). In the embodiment on the left where the implant is used to repair or replace a ligament that is attached to two bones 10, the hydrogel/polymer 110, 120 is interfaced with two porous rigid bases 130, one for each bone 10. In both of these embodiments, there are also more than one solid hydrogel/polymer 110 and more than one porous hydrogel/polymer 120. The solid hydrogel/polymer 110 and porous hydrogel/polymer 120 are layered in this particular embodiment. The purpose of this is to allow for cellular ingrowth into the porous hydrogel/polymer while the solid hydrogel/polymer provides the necessary tensile mechanical forces. This type of configuration can be used for other musculoskeletal tissue.

This embodiment of the implant can be manufactured by either alternating layers of porous hydrogel/polymer and solid hydrogel/polymer and then crosslinking the layers by freeze/thaw or other methods, or by inserting the solid hydrogel/polymer into the porous hydrogel/polymer impregnated degradable sponge prior to the digestion of the sponge.

Figure 1E:
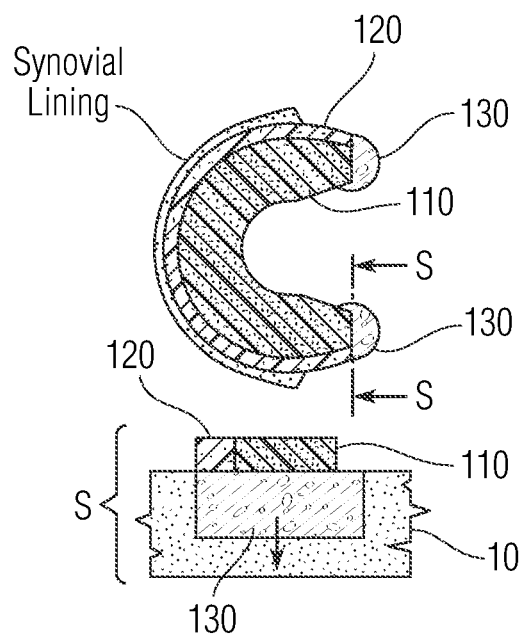
FIG. 1E is a schematic illustrating the use of the implant to treat, repair or replace meniscus tissue.

FIG. 1E is a schematic of a further embodiment of the implant 100 for use in the meniscus. In this embodiment, there is one porous hydrogel/polymer layer 120 surrounding a solid hydrogel/polymer 110 attached on either end to a porous rigid base 130.

Figure 1F:
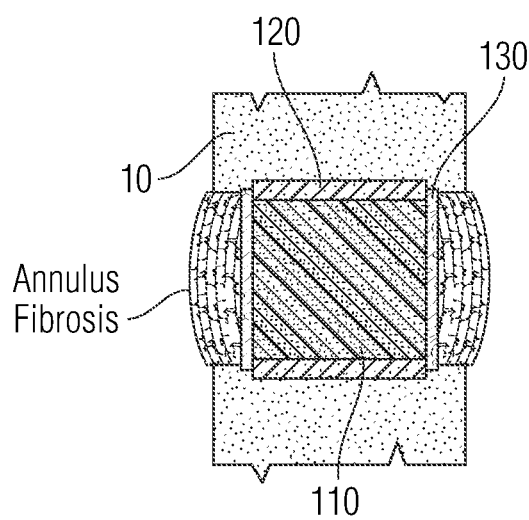
FIG. 1F is a schematic illustrating the use of the implant to treat, repair or replace spinal discs.

FIG. 1F depicts the use of the implant to treat, repair or replace spinal discs. In this embodiment, one relatively large solid hydrogel/polymer 110 has two porous hydrogel/polymer layers 120 and is interfaced with two relatively small porous rigid bases 130, which mimics spinal discs in structure and function.

As can be seen from the exemplified embodiments, there are many types of musculoskeletal tissue in which the multi-component implant can be implanted. While FIGS. 1B-1F show specific embodiments of the implant 100 for specific musculoskeletal tissue, one of skill in the art can determine the size and number and configuration of the various components (solid hydrogel/polymer 110, porous hydrogel/polymer 120, and porous rigid base 130) of the implant 100 based upon the structure and function of the musculoskeletal tissue to be treated, repaired or replaced. In addition, as shown in FIG. 1D, the implant of the current invention can be used to replace musculoskeletal tissue in its entirety and not just to treat, repair or replace a defect or injury.

While it has been previously suggested that a non-porous hydrogel layer combined with a porous base (U.S. Pat. No. 5,314,478) would make for a suitable osteochondral implant, there are specific and unique aspects of the present implant design that are not present in the prior art and include:

a. The porous rigid base 130 is interfaced with the solid hydrogel 110 and the porous hydrogel 120. The solid hydrogel 110 (e.g. a solid core) resists deformation and transmits the load to the porous rigid base 130, while the porous layer 120 of the implant 100 as well as the porous rigid base 130 enables cellular migration from the surrounding tissue into the implant 100 and matrix generation within the pores, thereby enabling simultaneously integration from both the cartilage and bone (which is not possible using U.S. Pat. No. 5,314,478 due to the non-porous design of the hydrogel layer).

b. The interface between the hydrogel 110, 120 and the porous rigid base 130 is designed to maximize integration between these very different layers; specific geometric features (macro- and micro-porous holes) combined with use of an intermediate layer of low viscosity polymer solution, at the time of manufacture, are required to prevent hydrogel-porous rigid base separation.

c. Both the porous and non-porous hydrogels 110 120 are dehydrated prior to implantation, then rehydrated when in the biological environment of the site of the defect or injury. The initial dehydration reduces the size of and stiffens the hydrogels and enables the device 100 to be pushed into the defect site at the time of implantation. After the hydrogel rehydrates within the site of implantation, the hydrogel 110, 120 expands to ensure that the implant 100 fills the defect site.

d. The dehydration-rehydration process can allow for the inclusion of supplemental agents in the implant at the time of surgery.

e. The porous rigid base 130 has a unique gradual taper to enable ease of implantation into the defect site.

f. The solid hydrogel 110 and porous rigid base 130 "carry" joint loads by ensuring that the surface of the implant 110 is contiguous and proud to the articular surface of the adjacent tissue.

For a preferred embodiment of the implant of the present invention (designed for use to treat, repair or replace an osteochondral defect), the ultimate shear stress at the hydrogel 110 120 and porous rigid base 130 was determined to be 0.4 MPa and the tensile stress required to separate the hydrogel 110 120 and porous rigid base 130 was found to be 0.22 MPa. See Example 7 and FIGS. 8A and 8B. One of skill in the art will understand that the value for the ultimate shear stress and ultimate tensile stress of the interface will vary depending on the tissue type to be repaired as well as the forces that the interface must resist, but this data show that the implant of the current invention can withstand the forces necessary to be used in treatment, repair and replacement of musculoskeletal tissue.

Figure 12:
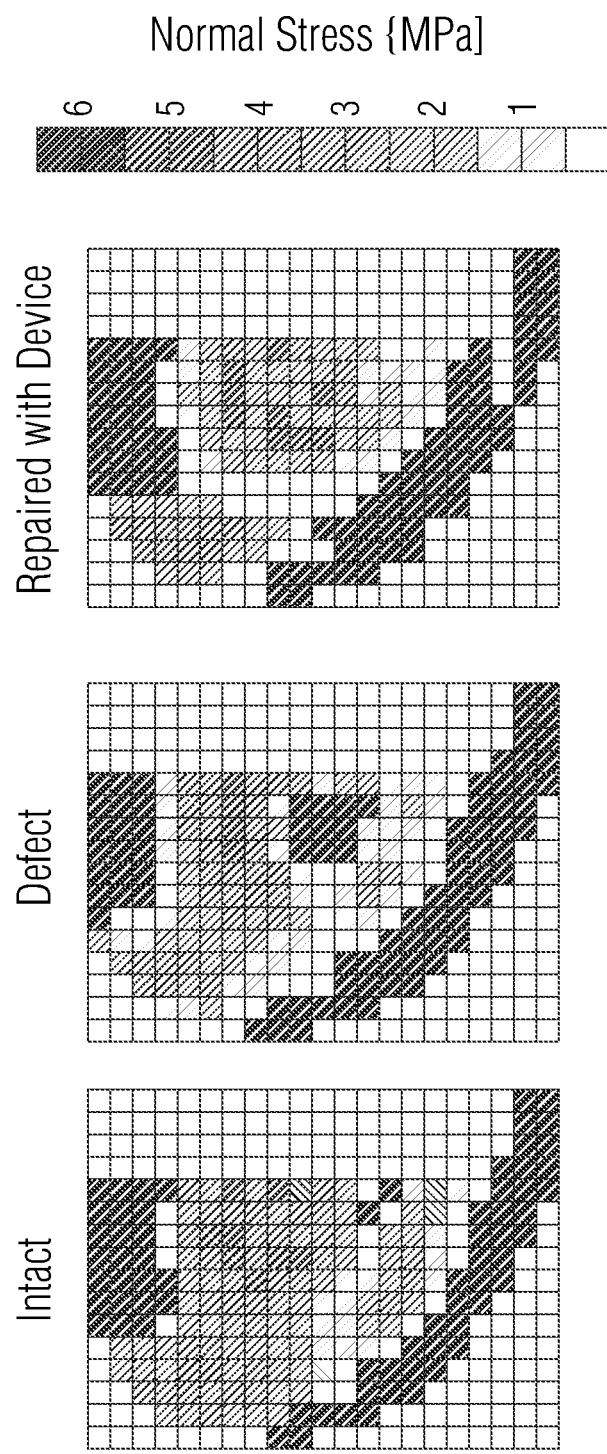
FIG. 12 show stress sensor readings from the tibial plateaus of cadaver knees. Reading were taken when they were intact, with a defect, and repaired with the device of the present invention.

Moreover, the implant 100 of the present invention comprising the solid hydrogel/polymer 110, the porous hydrogel/polymer 120 and the porous rigid base 130 were found to restore normal joint loading. See Example 8 and FIG. 12.

As stated, the implant of the present invention comprises three components: the solid hydrogel 110, the porous hydrogen layer 120, and the porous rigid base 130.

The Solid Hydrogel/Polymer

The solid hydrogel/polymer 110 can be made from any non-biodegradable polymer. While polyvinyl alcohol or PVA is preferred, any non-biodegradable polymer which has mechanical properties that can be controlled separately by varying the polymer concentration and/or the method of polymerization can be used including but not limited to, polyvinyl pyrrolidone, polyacrylamide, polyethylene glycol, polyurethane, and combinations thereof.

It will be understood by those in the art that the solid hydrogel 110 will have little to no porosity and be able to resist deformation and transmit the load to the porous rigid base.

In its dehydrated form, the solid hydrogel 110 can change in shape, size, and stiffness providing support during insertion of the implant. In addition, the solid hydrogel 110 upon rehydration will swell with joint fluid providing lubrication with any opposing surfaces.

The Porous Hydrogel/Polymer

The porous hydrogel/polymer 120 also can be made from any non-biodegradable polymer, in such a way that the material contains pores.

While polyvinyl alcohol or PVA is preferred, any non-biodegradable polymer which has mechanical properties that can be controlled separately by varying the polymer concentration and/or the method of polymerization can be used including but not limited to, polyvinyl pyrrolidone, polyacrylamide, polyethylene glycol, polyurethane, and combinations thereof. In some embodiments, the porous hydrogel layer 120 surrounds the solid hydrogel 110 (see FIGS. 1A, B, C, E, and F). In other embodiments, the solid hydrogel and the porous hydrogel are in layers (see FIG. 1D). In every embodiment, the porous hydrogel/polymer is adjacent to the solid hydrogel/polymer.

Another important aspect of the present invention is that the implant 100 must have the ability to be integrated into the tissue. This is achieved by surrounding cells integrating into the construct upon implantation into the body. This is achieved in part by the porous hydrogel layer 120 which is porous and has a pore size large enough to allow cells to infiltrate the porous hydrogel. Allowing cells to integrate with the porous hydrogel/polymer creates an environment with more uniform loading at the tissue-implant interface preventing cell death.

A chondrocyte is 10 to 30 µm in diameter. Thus, a construct with a pore size larger than 10 µm would allow for migration and infiltration of these cells. In order for fibrochondrocytes to move into and through a material, pore sizes of about 100 to about 300 µm are required. The optimal porosity for musculoskeletal tissue repair is 50% to 90% porosity however, porosity for the construct can range from 0% to 99% porous depending on the application. The porosity of the porous hydrogel 120 is determined by site of the injury and can be easily modified by the person of skill in the art in order to obtain optimum porosity.

Figure 2A:
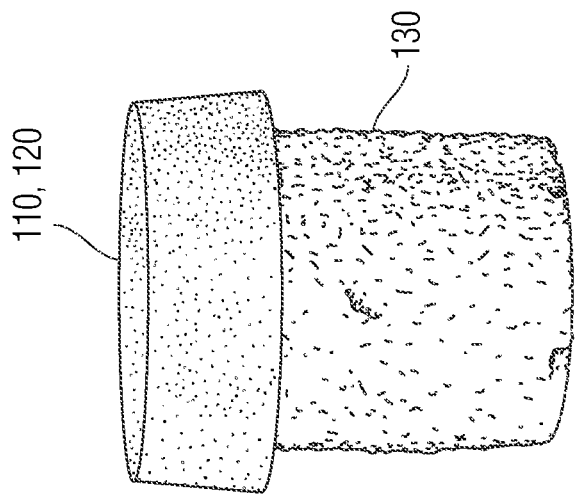
FIG. 2A illustrates an implant with a dehydrated hydrogel portion and FIG. 2B illustrates the implant with a rehydrated hydrogel portion. The dehydrated hydrogel attached to the rigid porous base is a trapezoidal shape. The rehydrated hydrogel is larger than the defect or injury to create a press-fit with the edges of the injury or defect.
Figure 2B:
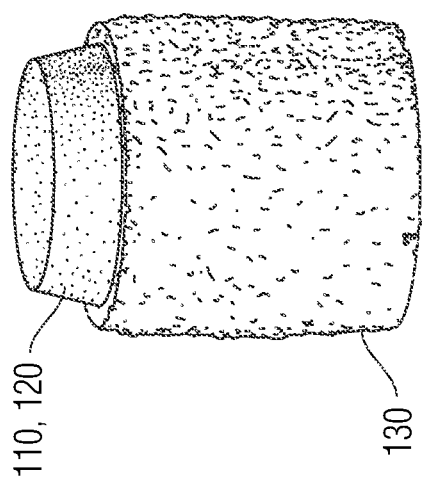

A further unique feature of the hydrogel/polymer portions 110, 120 of the implant 100 (i.e., the solid hydrogel 110 and the porous hydrogel 120) is that they can be dehydrated and reduced in size prior to implantation. Dehydration of the implant 100 creates a unique geometry for easy implantation with shrinkage of both the solid hydrogel and porous hydrogel (top layer diameter) 110, 120, and no change in the dimensions of the porous rigid base 130, together which can form a trapezoidal shape (FIG. 2A). After implantation, the hydrogel layer 110, 120 will expand to fill the defect (FIG. 2B).

These geometric changes facilitate: (i) implantation of the device 100; (ii) addition of supplemental agents at the time of implantation; and (iii) expansion of the solid and porous hydrogel 110, 120 to fully fill the defect sealing off the margins of the defect from fluid flow that may cause cysts in the bone or other tissue.

Figures 3A, 3B:
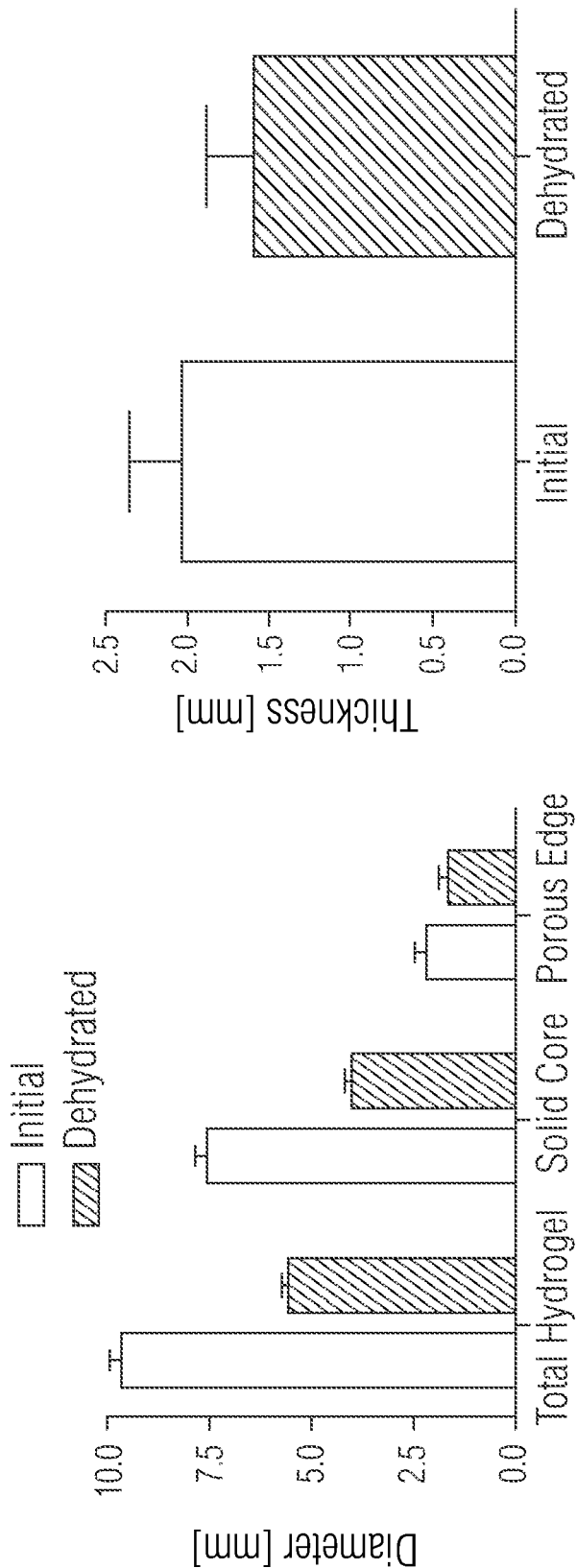
FIGS. 3A and 3B are graphs of the quantification of the changes in the hydrogel portion of an implant (total hydrogel, the solid hydrogel and porous hydrogel edge) in diameter (FIG. 3A) and thickness (FIG. 3B) after dehydration represented as the mean and standard deviation.

In one quantification of the changes in hydrogel diameter after dehydration show about a 44% decrease in diameter at the top surface and about a 31% decrease in diameter at the bottom surface from the initial size of the hydrogel (FIG. 3A). There was a smaller change in the height of the hydrogel 110, 120 with about a 22% decrease in thickness from the pre-dehydrated thickness (FIG. 3B). See Example 4. Optimal changes in the hydrogel size is about 10% to 50% of its original size however, the decrease in the length, width and thickness of the hydrogel can be altered by changing the porosity of the hydrogel, crosslinking of the polymer chains, and/or rate of evaporation of the aqueous phase.

Since the hydrogel portion of the device 100 was designed to create a press-fit with the surrounding native tissue, dehydration facilitates implantation of the device by making the diameter of the hydrogel smaller than the size of the defect into which it will be implanted. Initial fixation of the device 100 is through the porous rigid base-bone interface. However, hours after implantation, the hydrogel portion 110, 120 of the device 100 will have fully rehydrated, so that cartilage-hydrogel integration can occur.

Once dehydrated, the hydrogel surface layer is stiffer than in the hydrated state, thus allowing the top hydrogel surface to be pressed into the defect site at the time of surgery.

Figure 4B:
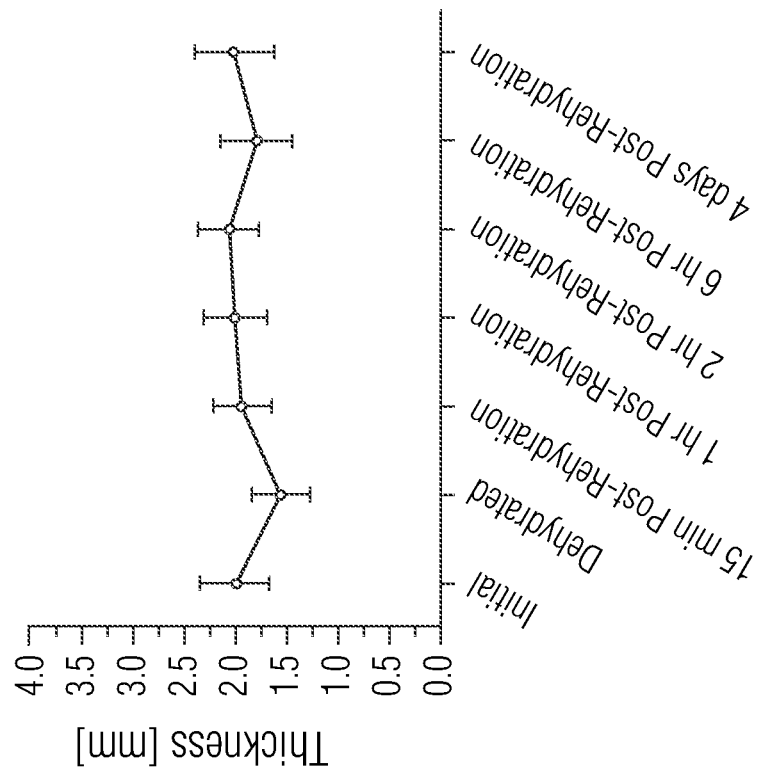
FIGS. 4A and 4B are graphs showing the quantification of the changes in the hydrogel portion of an implant, the total and the solid hydrogel, in diameter (FIG. 4A) and thickness (FIG. 4B) after dehydration and 15 minutes, 1 hour, 2 hour, 6 hour and 4 days after rehydration. The differences in the rate of rehydration between the solid hydrogel and porous hydrogel periphery or layer can be visualized in the hatched region of FIG. 4A, with a larger gap between the total (solid hydrogel and periphery hydrogel) and solid hydrogel indicating a faster rate of rehydration of the porous periphery. Little difference can be seen in the thickness of the hydrogel during rehydration.
Figure 4A:
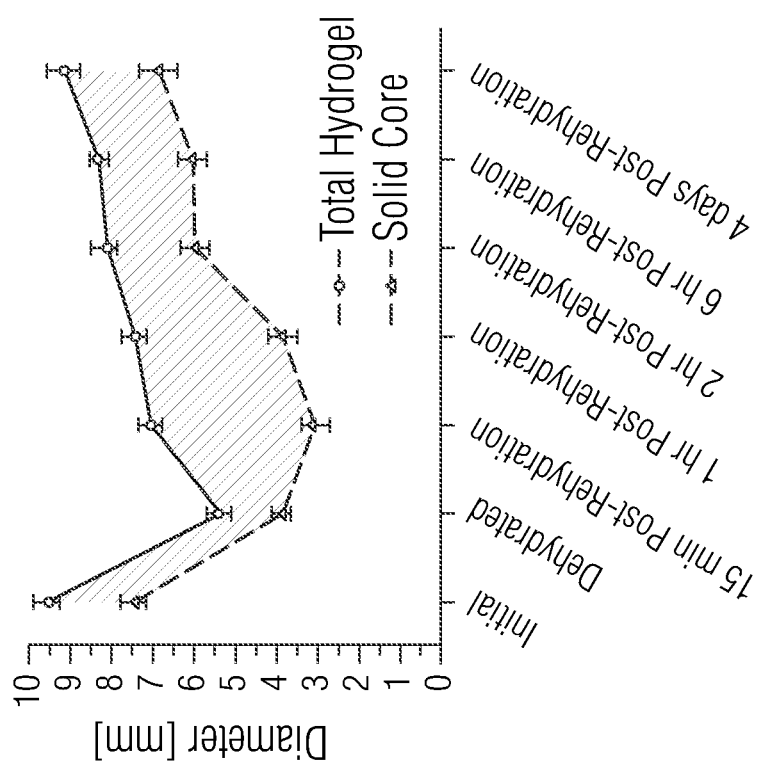

The rehydration times for the implants were characterized as shown in Example 5 and FIGS. 4A and 4B. The solid hydrogel 110 and porous hydrogel layer 120 of the implant 100 rehydrated at different rates with the solid hydrogel rehydrating in about 2 hours and the porous hydrogel layer 120 fully rehydrating in about 1 hour.

Based upon work performed by Ng et al. 2012, the optimal press fit is between about 8% and about 40% interface interference. The percent interface interference is dependent on the stiffness of the hydrogel material and can be determined by those of skill in the art. For the hydrogel portion 110, 120 of the implant 100 made in Example 1, about a 15% interference between the defect and the hydrogel was found to give the best implant/cartilage edge integration. Characterization of the hydrogels from Example 1 from their initial hydrated, dehydrated and rehydrated states showed an approximately 46% decrease in the size of the hydrogels from initial hydrated to dehydrated states, and an approximate 8% decrease in the size of the hydrogels from initial hydrated to fully rehydrated state. This information was used to create hydrogels that were initially 8% larger than the desired 15% interference fit (e.g., initial hydrated hydrogel size of 10 mm in diameter with a final rehydrated size of 9.20 mm in diameter that will be placed into an 8 mm defect). However, using the 10 mm diameter hydrogel, the average rehydrated diameter of the PVA hydrogel was 9.10 mm giving an interference fit of about 13.75%. Using these guidelines, parameters, and the size of defect, a person of skill in the art can determine the initial size to make the final hydrogel portion of the implant based upon the final desired size of the implant and the change in size when the hydrogel is dehydrated and rehydrated.

Figure 5:
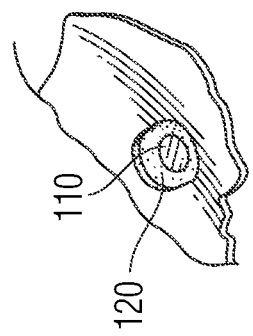
FIG. 5 is a view post implantation of the device in a defect created in a rabbit trochlea. The porous hydrogel in the periphery filled with blood and marrow from subchondral bleeding.

In addition, since the rate of rehydration of the solid hydrogel 110 differs from that of the porous hydrogel 120, this allows time for the porous hydrogel 120 to rehydrate with the patient's own fluids or pre-hydrated with agents such as blood, platelet rich plasma, or proteins, which can contain growth factors that may facilitate cell migration into the porous hydrogel. As shown in FIG. 5, the porous hydrogel periphery fills with blood as it rehydrates and expands, while the solid hydrogel remains dehydrated.

The hydrogel portion of the implant (the solid hydrogel (e.g., a core) and porous hydrogel) can manufactured by the novel method set forth below and in co-owned U.S. Pat. No. 8,557,270, herein incorporated by reference, or by any method known in the art.

The Porous Rigid Base

The porous rigid base 130 of the current implant 100 has three functions, it carries load, provides initial fixation for the hydrogel layer in the tissue, and enables cellular migration from the surrounding tissue into the implant 100 for matrix generation within the pores, thereby enabling simultaneously integration from both the cartilage and bone.

The porous rigid base 130 may be made from any material that is strong enough to carry load in the site of the injury or defect, and is porous. Preferred material for the porous rigid base 130 includes but is not limited to bone, metal, polyetherketoneketone (PEKK), polyetheretherketone (PEEK), and bioactive glass (e.g., silicone oxide, sodium oxide). This porous rigid base 130 should have walls which contain micropores ranging from about 150 to 500 µm in diameter.

The porous rigid base 130 can also have many different features, including but not limited to, a step at the hydrogel-base interface and macroporous structures to improve mechanical interlock between the two layers, and a taper on the bottom of the porous rigid base 130 to allow alignment of the device 100 with the defect.

The first unique aspect of the present invention is the interface between the hydrogel and the porous rigid base designed to maximize integration between these very different layers. This interface uses specific geometric features (e.g., macro- and micro-porous holes and steps) combined with use of an intermediate layer of polymer, such as poly(vinyl) alcohol, poly(vinyl) pyrrolidone, or other liquid polymer solutions.

Figure 6B:
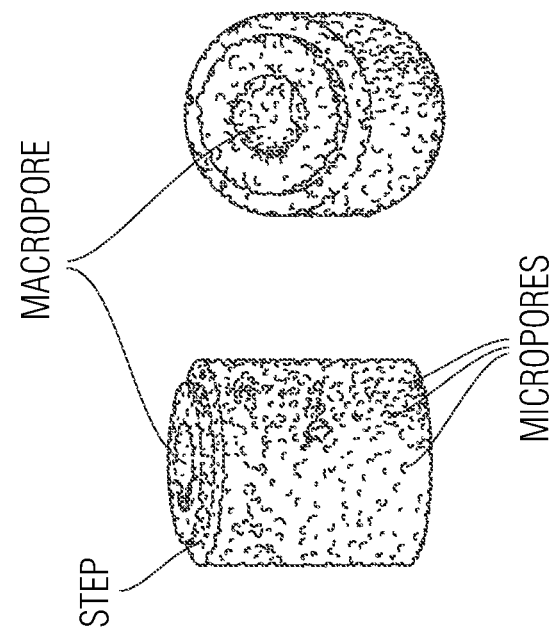
FIG. 6B is an image of a porous rigid base showing the step, the macropores added to the base, and the micropores throughout the base.
Figure 6A:
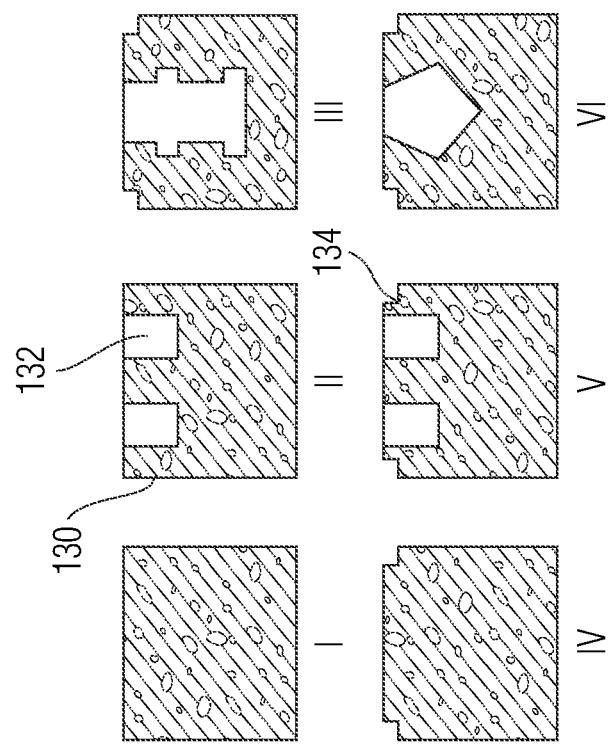
FIG. 6A depicts drawings of samples of configurations of the porous rigid base.

FIGS. 6A and 6B show sample configurations. FIG. 6A Example II shows the porous rigid base 130 with an extension 132 to the surface area of the base with the inclusion of macroporous structures. Example IV demonstrates the addition of a step 134 in the porous rigid base 130, and Examples III, V, and VI show possible variations in the design of the macroporous structures. Macropores can range in size from about 1% to 90% of the surface of the porous rigid base in diameter and from about 10% to 50% of the porous rigid base depth. For one embodiment of the implant used for treatment and repair of osteochondral defects, a porous rigid base with a single macropore with dimensions of about 2 to 4 mm in diameter and about 1 to 5 mm in depth in the center is used. Porous rigid bases with more than one macropore can be used with the macropores ranging in size from 1 to 2 mm in diameter and 1 to 3 mm in depth.

Figures 7A, 7B:
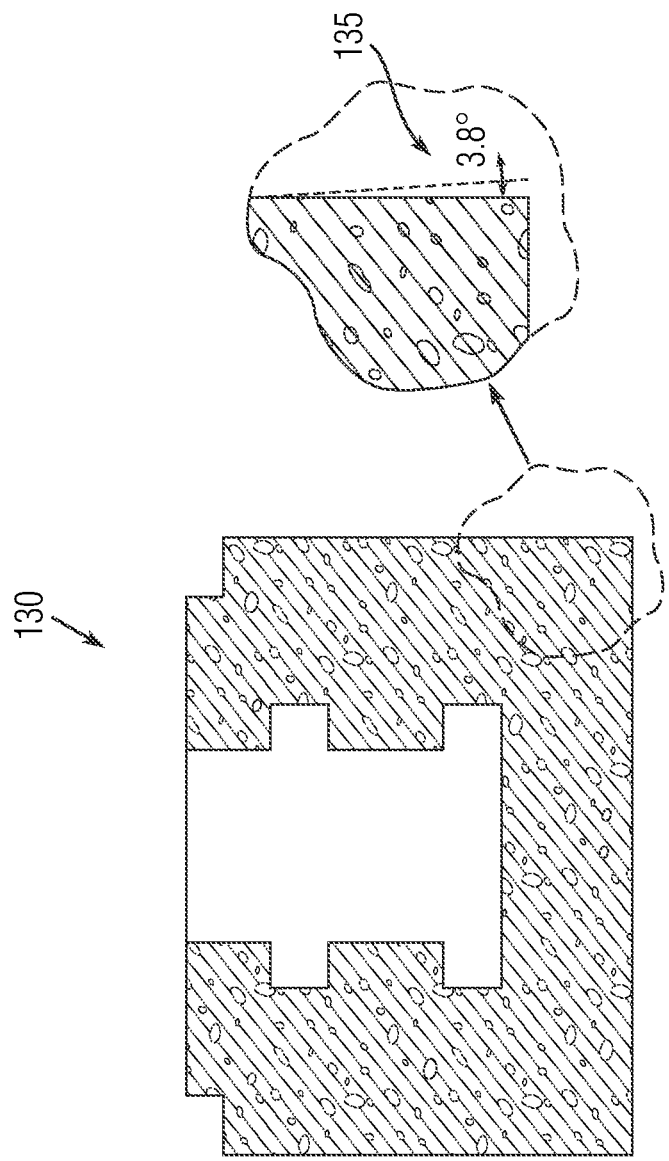
FIGS. 7A and 7B depict the porous rigid base with a taper at the bottom of 3.8° taper to facilitate alignment during implantation.

Another unique aspect of the porous rigid base 130 is that it is shaped in a slight, but long taper (shown at 135 in FIG. 7A) to facilitate insertion. The base of the porous rigid base 130 can be tapered from about 1° to about 10° with about 3.8-4.0° being most preferred. This is done to facilitate insertion of the implant (FIGS. 7A and 7B). This taper 135 allows for self-alignment of the implant 100 with the edges of the defect thereby preventing misaligned implantation of the device 100.

For use in bone, the porous rigid base must be osteoinductive, meaning it has an affinity for bone ingrowth.

Supplemental Agents

Other agents can be optionally added to the implant 100, either externally or internally. Any agent that facilitates migration, integration, regeneration, proliferation, and growth of cells into and around the implant, and/or the injury or defect, and/or promotes healing of the injury or defect, and/or are chondrogenic and osteogenic, i.e., build bone and cartilage, can be added to the implant.

These agents include, but are not limited to, cytokines, chemokines, chemoattractants, anti-microbials, anti-virals, anti-inflammatories, pro-inflammatories, bone or cartilage regenerator molecules, blood, blood components, platelet rich plasma, and as combinations thereof, specific for the injury or defect being treated, repaired, and/or replaced. Addition of these components can be performed by soaking the dehydrated hydrogel in the agent for about 15 minutes prior to implantation to allow the porous hydrogel to rehydrate with the agent. The implant can then be delivered as described below into the defect with the agent in the porous hydrogel.

Cytokines for use in the invention include, but are not limited to, interleukins (e.g., IL-13), interferons, transforming growth factor (TGF), epidermal growth factor (EGF), insulin growth factor (IGF), fibroblast growth factor (FGF), vascular endothelial growth factor (VEGF), dermal growth factor, stem cell factor (SCF), granulocyte-colony stimulating factor (G-CSF), granulocyte-macrophage stimulating factor (GM-CSF), stromal cell-derived factor-1, steel factor, platelet derived growth factor (PDGF), angiopoeitins (Ang), hepatocyte growth factor, insulin-like growth factor (IGF-1), colony-stimulating factors, thrombopoietin, erythropoietin, fit3-ligand, and tumor necrosis factor α (TNFα) as well as combinations thereof.

Chemokines include, but are not limited to, CC, CXC, C, and $CX_3C$ chemokines.

Chemoattractants include, but are not limited to, bone morphogenic protein (BMP), fibroblast growth factor (FGF), and transforming growth factor (TGF).

These chemokines, cytokines, and chemoattractants will have the ability to stimulate cell migration, proliferation, and regeneration around and into the defect or injury, as well as promote adhesion, and synthesis of the extracellular matrix.

Anti-microbial agents include, but are not limited to, 3-lactam antibiotics, such as cefoxitin, n-formamidoyl thienamycin and other thienamycin derivatives, tetracyclines, chloramphenicol, neomycin, gramicidin, bacitracin, sulfonamides, aminoglycoside antibiotics such as gentamycin, kanamycin, amikacin, sisomicin and tobramycin, nalidixic acids and analogs such as norfloxican, the antimicrobial combination of fluoroalanine/pentizidone, and nitrofurazones.

Anti-inflammatory agents are agents that inhibit or prevent an immune response in vivo. Exemplary anti-inflammatory agents include: agents which inhibit leukocyte migration into the area of injury ("leukocyte migration preventing agents"); and antihistamines. Representative leukocyte migration preventing agents include, but are not limited to, silver sulfadiazine, acetylsalicylic acid, indomethacin, and Nafazatrom. Representative anti-histamines include, but are not limited to, pyrilamine, chlorpheniramine, tetrahydrozoline, antazoline, and other anti-inflammatories such as cortisone, hydrocortisone, beta-methasone, dexamethasone, fluocortolone, prednisolone, triamcinolone, indomethacin, sulindac, its salts and its corresponding sulfide.

Pro-inflammatory agents would be added to an implant or patch when the generation of scar tissue is desired to increase the stability of the implant, such as when the implant is being implanted into a fascia defect or the annulus to allow healing of scar tissue in a controlled manner.

Additional agents that can be included or added to the patch or implant could include, for example: aminoxyls, furoxans, nitrosothiols, nitrates and anthocyanins; nucleosides, such as adenosine; and nucleotides, such as adenosine diphosphate (ADP) and adenosine triphosphate (ATP); neurotransmitter/neuromodulators, such as acetylcholine and 5-hydroxytryptamine (serotonin/5-HT); histamine and catecholamines, such as adrenalin and noradrenalin; lipid molecules, such as sphingosine-1-phosphate and lysophosphatidic acid; amino acids, such as arginine and lysine; peptides such as the bradykinins, substance P and calcium generelated peptide (CGRP), and proteins, such as insulin, vascular endothelial growth factor (VEGF), and thrombin.

Other agents can include pharmaceutically active compounds, hormones, enzymes, DNA, plasmid DNA, RNA, siRNA, viruses, proteins, lipids, pro-inflammatory molecules, antibodies, anti-sense nucleotides, and transforming nucleic acids or combinations thereof.

Adhesives may also be added to the implant. One particular preferred adhesive are those disclosed in commonly-owned U.S. Pat. No. 8,440,618, which is incorporated by reference in its entirety. Such adhesives are chemical and biological moieties having the ability to bind to a component of the extracellular matrix of the host tissue upon implantation. Upon implantation, the moiety of the composition would allow the implant to integrate with the extra-cellular matrix components of the host tissue in a short period of time. In a preferred embodiment, the moiety would bond with collagen, thus, any tissue that contains collagen in its extracellular matrix is a candidate for implantation of the composition.

In a preferred embodiment, the moiety is chemical, and in a most preferred embodiment, contains a chemically reactive group, such as a carbonate ("open carbonate" or "OC").

In another preferred embodiment, the moiety is biological. Biological moieties would be derived from living organisms or through protein engineering, and could include, but are not limited to, proteins, protein sub-domains, and mutated proteins with altered affinity for a ligand, in particular, collagen. One source for biological moieties would be bacteria, including but not limited to *Staphylococcus aureus, Enterococcus faecalis*, and *Streptococcus nutans*. Other sources would be mammalian collagen binding proteins, such as decorin. A preferred biological moiety is a protein derived from *Staphylococcus aureus*, encoded by the collagen adhesion gene, CNA.

The implant can also comprise agents that increase the strength of the solid hydrogel including but not limited to, polymer fibers, carbon nanofibers, free radicals (to enhance crosslinking), and hydrogel chemistry modification agents.

Exemplary Method of Manufacture

To obtain the implant meeting the criteria set forth above, the method of manufacture can comprise at least the following steps:
1. preparation of the hydrogel/polymer portion 110, 120 of the implant 100, both the solid portion 110 and the porous portion 120, preferably from a interconnected sponge made of or containing a degradable or biodegradable polymer;
2. preparation of the porous rigid base 130 by creating geometric features such as macropores and steps, and filling the geometric features, e.g., macropores, with a non-biodegradable polymer;
3. assembling the implant 100 by placing the hydrogel portion 110, 120 onto the top surface of the porous rigid base portion 130 and cross-linking the hydrogel 110, 120 to the polymer in the porous rigid base 130;
4. removal of the biodegradable or degradable polymer from the sponge in the hydrogel portion 110, 120 of the implant 100 to form macroporous network in at least a portion of the hydrogel portion 120 of the implant 100; and
5. dehydration of the hydrogel portion 110, 120 of the implant 100.

Preparation of the Hydrogel Portion of the Implant

The preparation of the hydrogel/polymer portion 110, 120 of the implant 100 can be manufactured by the method disclosed and claimed in co-owned U.S. Pat. No. 8,557,270.

Figure 9:
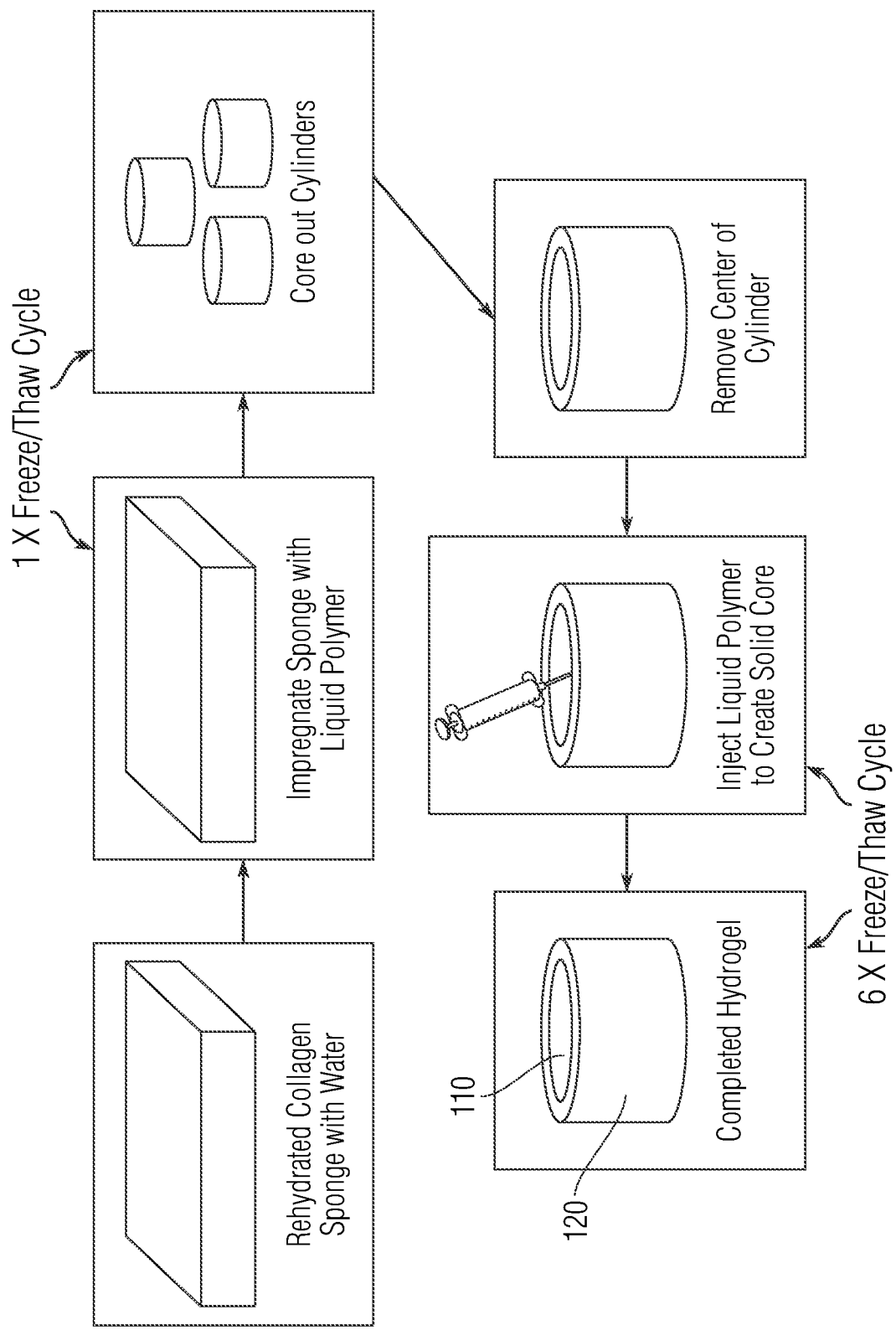
FIG. 9 is a schematic of one process for manufacturing the hydrogel portion of the implant.

The hydrogel portion 110, 120 of the implant 100 is preferably prepared using an interconnected sponge which is made of or contains a biodegradable polymer. The sponge is first hydrated and then the water is replaced with non-biodegradable polymer solutions, cross-linking the non-biodegradable polymer, coring the sponge, filling the sponge with a non-biodegradable polymer solution, and cross-linking the non-biodegradable polymer in the solid hydrogel (core). This process is generally shown in FIG. 9.

Gelatin sponges, which are the preferred starting material, are sterile absorbable gelatin products used to control bleeding. They are available commercially from Ethicon-Johnson & Johnson, Pfizer, Baxter, and Medtronic. The sponge can also be made of or contain other biodegradable polymers including, but not limited to, collagen, poly(lactic acid), poly(glycolic acid), chitosan, and alginate or degradable substance such as salts and polyethylene glycol.

Moreover the sponge's size, porosity and wall thickness can be varied depending on the needs of the final implant.

The sponge is hydrated by soaking it in deionized water for 1 hour to 5 days, with about 12 hours being preferred. A person of skill in the art would easily be able to determine a sufficient amount of time wherein the sponge is saturated with water.

The sponge is then centrifuged to remove the trapped air bubbles. The preferred method is at 3000 g for 1 hour at a time, 3-5 times, with gentle agitation between the centrifugations to restore the original shape. However, a person of skill could easily determine the extent of centrifugation necessary to remove air bubbles from the sponge. Another technique is the intermittent application of a vacuum for 30 minutes on and 30 minutes off, with agitation between the vacuum steps, for 3-5 times.

The next step in the method of the invention is replacement of the water in the sponge with poly(vinyl) alcohol or PVA. While PVA is preferred, any non-biodegradable polymer which has mechanical properties that can be controlled separately by varying the polymer concentration and/or the method of polymerization such as freeze/thawing can be used.

The mechanical properties of the final device are determined by the final concentration of the PVA in the device. Generally, the higher the final concentration of PVA in the device, the stiffer the device. A device with a higher concentration of PVA can generally withstand a higher load.

The PVA is substituted into the sponge under gentle agitation in steps of increasing concentration up to the desired concentration. PVA solutions of varying concentration are made and the sponges soaked until the desired concentration is obtained. The PVA solutions range from 1% to 40% weight/volume solutions, up to the desired final concentration, with the preferred final concentration of PVA scaffolds ranging from 10% to 40%. The preferred final concentration will depend upon the final use of the scaffold, as determined by the person of skill. The preferred method is to soak the sponge from about 1% to about 5% PVA up to a final concentration of 10% PVA.

The PVA hydrogels are then subject to a series of freeze/thaw cycles. PVA offers the advantage of being physically cross-linked using freeze/thaw cycles, without the need for use of potentially toxic cross-linking agents. During freezing, water freezes and cause regions of high PVA cross-links to form. As the PVA chains come in close contact with one another, crystallite formation and hydrogen bonding can occur between the chains. These interactions remain intact following thawing, and thereby create a three-dimensional network. Thus, the mechanical properties of the hydrogel can be controlled by increasing the number of freeze/thaw cycles such that the amount of hydrogen bonding and crystallite formation can be increased. The increase in freeze/thaw cycles increases the strength of the construct. The mechanical properties can also be controlled by the duration and rate of freezing and thawing.

The preferred method involves freezing the construct at about −20° C. for about 20 hours and then thawing the construct at about 25° C. for about 4 hours. However, this part of the process can be easily varied by the person of skill in order to vary the mechanical properties of the construct as desired. Both the number of hours of freezing and/or thawing can be varied as well as the number of cycles. For example, the total number of freeze/thaw cycles can range from 1 to 8. The construct can be frozen at each interval for a time ranging from 4 to 24 hours, with 20 hours being preferred. The thaw time can range from 4 to 12 hours, with 4 hours being preferred.

While PVA is the preferred non-biodegradable polymer, and freeze/thawing the preferred method for cross-linking the PVA, other non-biodegradable polymers, and methods known in the art to cross-link such polymers, can be used.

Figure 10A:
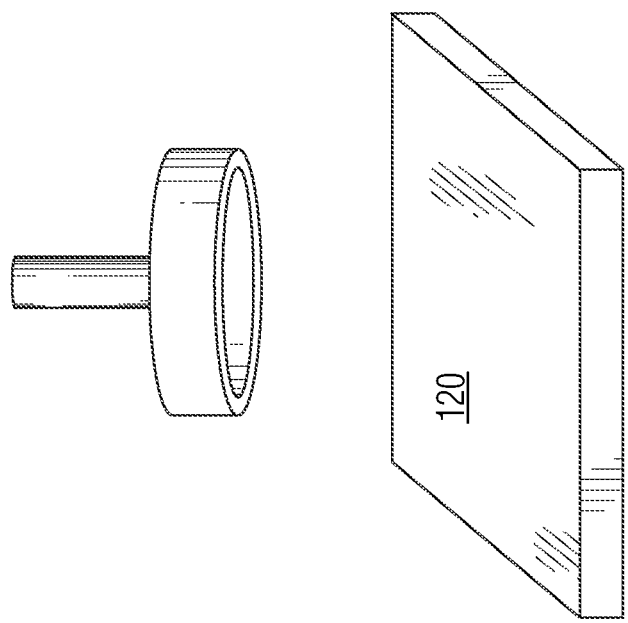
FIGS. 10A and 10B illustrate methods of making the hydrogel portion of one embodiment of the implant such that the porous layer is uniform around the solid hydrogel.
Figure 10B:
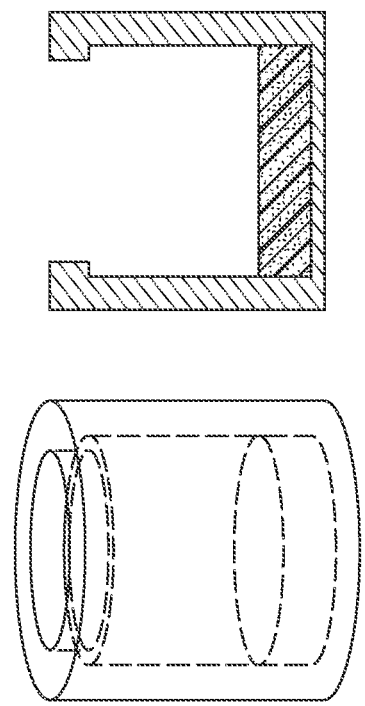

To obtain an implant with a solid hydrogel 110 in the center (a core), the center of the porous hydrogel is removed by any method known in the art. It is preferred that a customized centering jig as shown in FIG. 10A and Example 1 is used. However, a concentric cutting die shown in FIG. 10B can also be used. After the hydrogel material in the center is removed, it is filled with a liquid polymer and subjected to further cross-linking, preferably by additional freeze/thaw cycles. Again the number of freeze/thaw cycles can range from 1 to 8, with 6 being preferred. The liquid polymer that can be used is chosen from the group comprising polyvinyl pyrrolidone, polyacrylamide, polyethylene glycol, polyurethane, with polyvinyl alcohol being preferred.

After the freeze/thaw cycles are performed, the hydrogel portion can be trimmed to a desired size depending on the size of the defect or injury being replaced, repaired or treated. The preferable thickness of the final hydrogel portion ranges from about 0.5 mm to about 7 mm thick.

To obtain an implant with alternating layers of porous and solid hydrogel, the porous hydrogel is made using the method set forth above, and cut into sections. Additional polymer is added to some of the strips and additional crosslinking is performed, to obtain sections comprising a solid hydrogel. Then sections or strips of porous hydrogel and solid hydrogel can be alternated and crosslinked together using 3 to 8 freeze/thaw cycles. The alternating porous and solid hydrogel can then be trimmed to the desired thickness and length, with the thickness preferably ranging from about 0.5 mm to 0.7 mm thick and the length preferably ranging from about 1 mm to 5 mm long.

Preparation of the Porous Rigid Base

The porous rigid base 130 can be manufactured to contain many different features, including but not limited to, a step at the hydrogel-base interface and macroporous structures to improve mechanical interlock between the two layers, and a taper on the bottom of the porous rigid base to allow alignment of the device with the defect. FIGS. 6A-B and 7A-B show these features discussed above.

Preferred material for the porous rigid base includes but is not limited to, bone, metal, polyetherketoneketone (PEKK), polyetheretherketone (PEEK), and bioactive glass (e.g., silicone oxide, sodium oxide). This porous rigid base should contain micropores ranging from about 150 to 500 µm in size.

Macropores ranging from about 1% to 90% of the porous rigid base in diameter and from about 10% to 50% of the porous rigid base depth are created in the surface of the porous rigid base, which contains micropores, to further increase interdigitation between the hydrogel and the porous rigid base (FIG. 6B). For a preferred embodiment of the implant for osteochondral defects, a single macropore with dimensions of 2 to 4 mm in diameter and 1 to 5 mm in depth in the center of the implant can be used. Porous rigid bases with multiple macropores can also be created in the range of 1 to 2 mm in diameter and 1 to 3 mm in depth.

Assembly of Implant, Removing the Collagen Sponge and Dehydration

To create a robust interface that includes both the porous and non-porous components requires specific manufacturing and design specifications at that interface.

The macropores in the porous rigid base 130 are filled with a liquid polymer solution ranging from about 5% to about 20% polymer in deionized water. Polymers that can be used, include but are not limited to, polyvinyl pyrollidone, polyacrylamide, polyethylene glycol, and polyurethane, with polyvinyl alcohol being preferred. The thin layer of liquid polymer used to fill the macropores is then injected across the entire porous base using a syringe or other device. The liquid polymer is then infiltrated into the pores by pressurization. Pressurization can be accomplished by either displacing a known volume of polymer, applying positive pressure (e.g., a known weight to force the polymer into the porous rigid base), or by using negative pressure (e.g., a vacuum). This improves the interdigitation of the hydrogel with the porous rigid base.

Next the solid-porous hydrogel is placed onto the top surface of the porous rigid base with the liquid polymer. The assembled implant was then subject to any method that allows the hydrogel portion and liquid polymer interface to cross-link. A preferred method is physical crosslinking such as freeze/thaw cycling. See FIG. 11.

The collagen sponge can then be removed from the hydrogel portion of the implant by any technique including but not limited to, enzymatic digestion, and the entire implant is dehydrated prior to sterilization and implantation, which results in unique geometric changes in the hydrogel layer discussed above. This process allows the stiffer, dehydrated construct to be securely inserted into the defect at the time of surgery, while also ensuring that when the implant rehydrates it will expand to fill the site of the defect.

Exemplary Method of Implantation

Figure 14B:
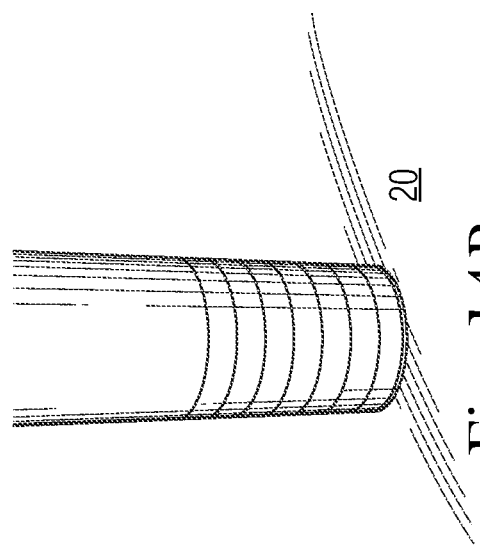
FIGS. 14B and C are representative arthroscopic views of the cartilage scoring instrument in use.
Figure 14C:
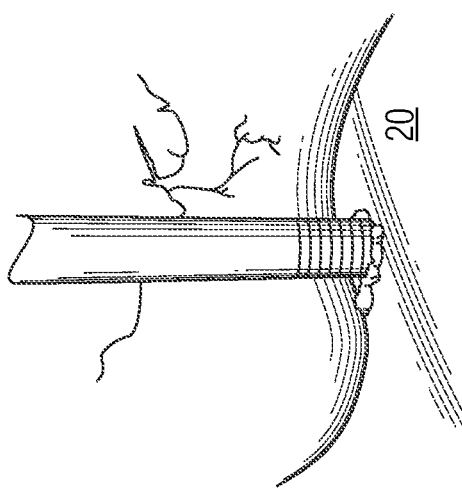
FIGS. 14A and B illustrate a system to cut and measure the thickness of the cartilage.
Figure 14A:
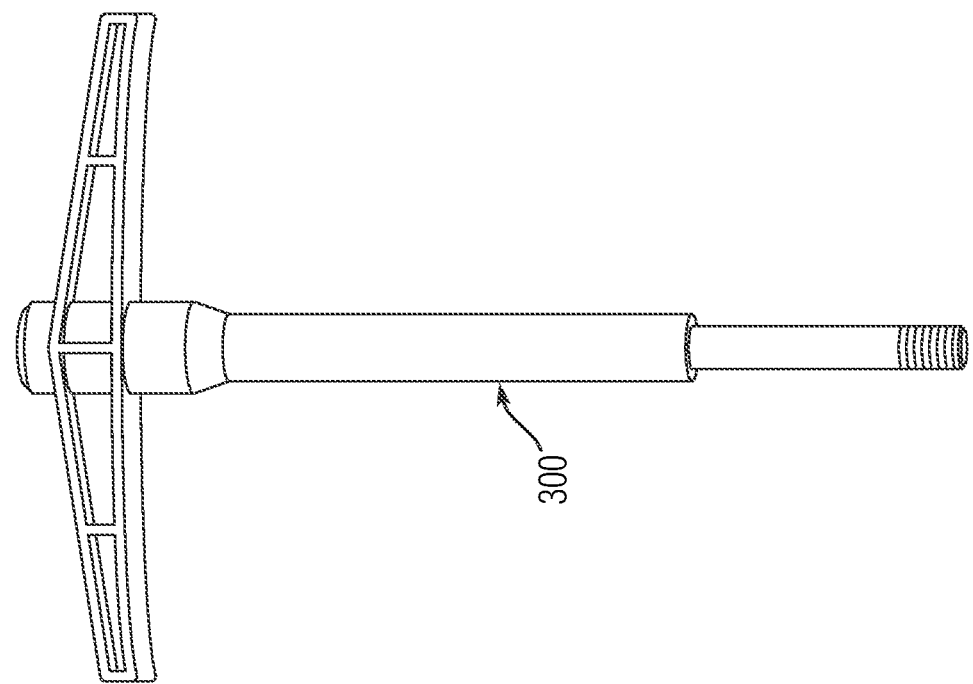

As discussed above, the mechanical function of the implant 100 is enhanced by the surface of the hydrogel being contiguous or slightly proud with the surface of the adjacent tissue where the implant is implanted. With this in mind, a method of implantation was devised to ensure that the surface of the hydrogel is properly aligned to the surface of the adjacent tissue. This method is as follows:

1. An alignment tool 200 (FIGS. 13A-D shows alignment tool 200 with inner cannula 210 formed therein) is placed on the surface of the tissue surrounding the defect or injury. Such alignment tool 200 is preferably curved to match the surface curvature of the tissue and is cannulated to allow a Kirschner wire 201 (K-wire) to pass through the cannula 210 of the tool 200 and be inserted into the tissue perpendicular to the tissue surrounding the defect or injury. Any method known in the art such as CT scans and MRI can be used to determine the surface topography of the tissue to obtain the alignment tool 200 with the proper curvature to match the tissue.
2. The edges of the defect or injury are scored. Preferably a tool (see tool 300 of FIG. 14A) is made that can be shuttled over the K-wire in such a way that it is concentric to the K-wire. The tool is then used to score the tissue surrounding the defect or injury to create a circular clean edge. The cutting can also be used to determine the thickness of the tissue, such as cartilage and thus, determine the appropriate thickness of the hydrogel portion of the implant to be used in the patient. FIGS. 14B and C show the scoring of the tissue using tool 300.

3. The tissue surrounding the defect or injury is drilled and the final depth of the defect or injury is measured (see FIGS. 15A-D showing the use of a reamer).
4. Based upon the two measurements, the size of the implant is chosen. The implant can optionally be partially rehydrated with an agent approximately 15 minutes before implantation.
5. The implant 100 is inserted into a tool with a delivery tube 400 and the delivery tube 400 is place over or around the defect or injury, or vice versa. A rod 420 is inserted into the delivery tube 400 and used to insert the implant 100 into the defect or injury by depressing the rod 420 into the tube 400. See FIGS. 16A-E.

In the case of an osteochondral defect, not only is the final depth of the defect measure (i.e., the bone and the cartilage), the thickness of the cartilage is also measured and matched to the thickness of the hydrogel portion of the implant keeping in mind the interface interference and the change in size of the dehydrated versus rehydrated implant as discussed above.

Tissue Treatment, Repair and Replacement

The implant 100 of the present invention can be used to treat, replace or repair defects and/or injuries in various musculoskeletal tissues, in a subject in need thereof, preferably a mammal, and most preferably a human. Musculoskeletal tissue contemplated to be treated, replaced or repaired includes bone, tendon, ligaments, cartilage, meniscus, and the discs of the spine. Those of skill in the art would appreciate that the implants of the present invention may be implanted into a subject using operative techniques and procedures, utilizing such techniques as magnetic resonance imaging and computer guided technology.

The implant 100 of the present invention can also be used to treat, replace or repair defects and/or injuries in other biological tissue, including but not limited to, arteries and blood vessels, and organs.

Kits

The present invention also includes kits, which could include the device 100 of the present invention, a tool for aligning (tool 200), a tool for cutting or scoring (tool 300), a tool (delivery tube 400) for insertion of the device 100 into the tissue, additional agents that can be added prior to implantation, and instructions for use, including determining the correct size of the implant and proper insertion.

For example, the device 100 of the present invention could be packaged in the kit by total defect depth and contain devices with different hydrogel heights ranging from 0.5 mm to 5.0 mm hydrogel height in increments of 0.5 mm. Preferably the hydrogel portion 110, 120 of the device 100 in the kit is dehydrated. The height of the porous rigid base 130 can be adjusted such that the total implant height remains constant for all devices included in the kit. The kit can include instructions for determining the correct size of the hydrogel 110, 120 based upon the general parameters of the change in size when the hydrogel 110, 120 in rehydrated.

The various tools to be included in the kit, e.g., alignment tool 200, cutting or scoring tool 300, and insertion tool 400, can be modeled after the ones used in Example 7.

The agents that can included to add to the implant prior to insertion or implantation are discussed in detail above and include but are not limited to cytokines, chemokines, chemoattractants, anti-microbials, anti-virals, anti-inflammatories, pro-inflammatories, bone or cartilage regenerator molecules, blood components, platelet rich plasma, and as combinations thereof, specific for the injury or defect being treated, repaired, and/or replaced.

EXAMPLES

The present invention may be better understood by reference to the following non-limiting examples, which are presented in order to more fully illustrate the preferred embodiments of the invention. They should in no way be construed to limit the broad scope of the invention.

Example 1—Manufacture of the Hydrogel Portion of the Implant

All handling and fabrication techniques were performed aseptically to minimize contamination with bacteria and other infectious agents.

A collagen sponge (Ethicon Surgifoam, Ref #: 1974) was soaked in deionized water overnight until the entire sponge was saturated with water via capillary action. The sponges were transferred to 50 mL conical tubes and repeatedly centrifuged at 3000 g for 1 hour at a time, with gentle agitation of the tube between centrifugations to restore its original shape, until all remaining air bubbles had been removed.

The sponge was then impregnated through increasing gradients of liquid polyvinyl alcohol (PVA) from 1% to 5%, up to the desired final concentration of 10% PVA. The impregnated collagen sponge was then subjected to one freeze/thaw cycle (20 hours at −20° C./4 hours at 25° C.).

Next the frozen impregnated sponge was cored using a cutting die, and the center of each core was removed using a cutting die and discarded. To ensure that the removed core is concentric with the outside walls, a customized centering jig was used as shown FIG. 10A. The center of the cylinder was filled with a liquid polymer (20% PVA) and subjected to another 6 freeze/thaw cycles.

After the freeze/thaw cycles the hydrogel portion of the implant was trimmed using a freezing-stage sledge microtome to the desired thickness.

Example 2—Manufacture of the Porous Rigid Base Portion of the Implant

A titanium (Ti6A14V or Ti6A14VELI) cylinder with a diameter of 9 mm and pores of about 150 to 500 µm in size and a 3.8% taper at the bottom, was drilled with one additional hole (1.3 mm diameter and 4.5 mm deep) at the top surface of the base. A 0.5 mm step was also created. These bases were designed using computer aided design and created using techniques such as electron beam melting or by laser metal sintering.

Example 3—Assembly of the Implant

Figure 11:
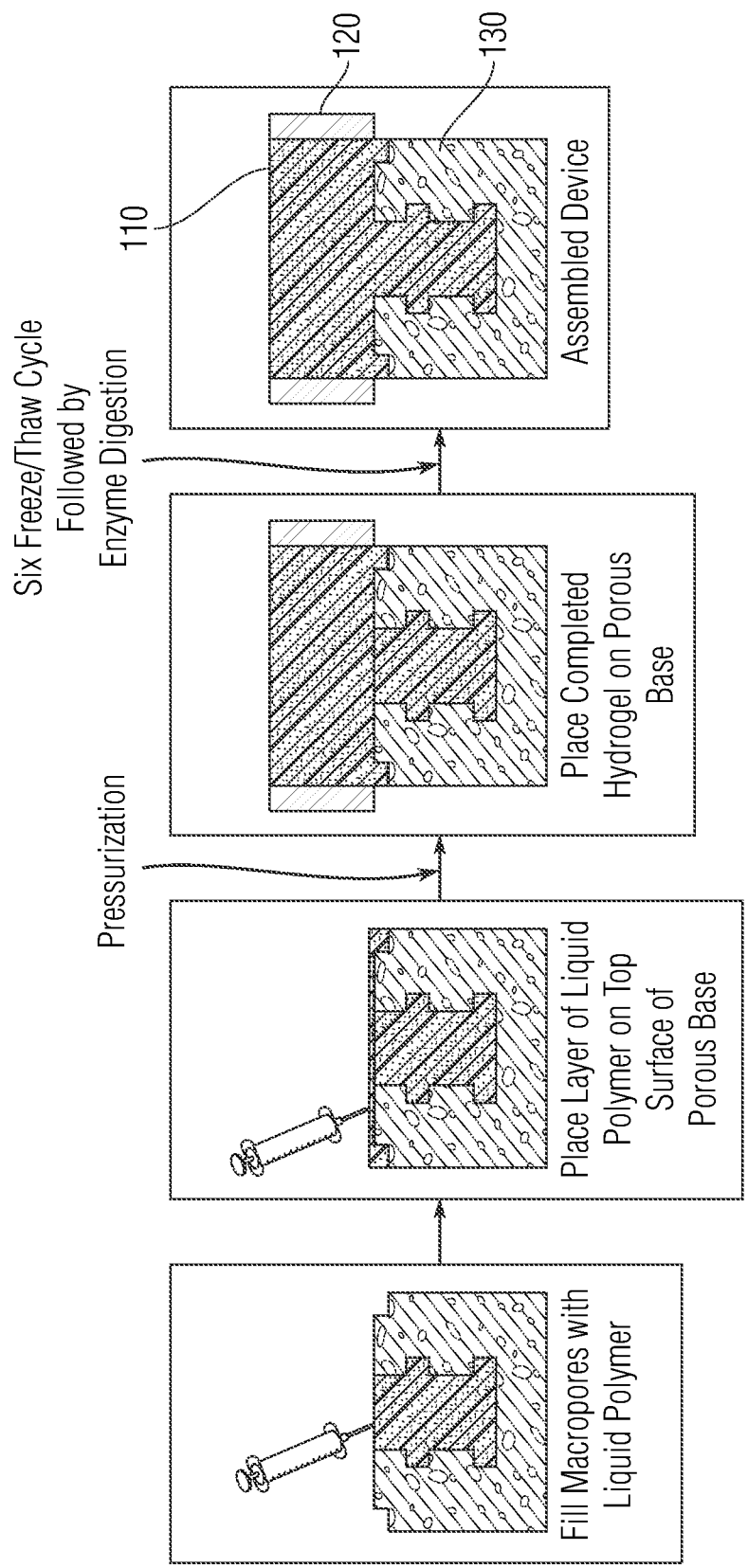
FIG. 11 is a schematic of one method for assembling the completed hydrogel layer with the porous rigid base.

As illustrated in FIG. 11, the macropores in the porous metal base from Example 2 were filled with a low viscosity PVA solution (10% or 1.33 molar PVA in deionized water), and a volume of 50 µL of 20% (or 2.67 molar) PVA was injected across the entire surface of the porous metal using a syringe. Positive pressure was applied using a known weight of 500 grams over 30 seconds to drive a 20% liquid PVA solution into the pores of the porous rigid base. The weight was removed and the solid-porous hydrogel from Example 1 was placed onto the top surface of the porous metal. The assembled implant was then subjected to 3 freeze/thaw cycles (−20° C. for 20 hours/40° C. for 4 hours)

to crosslink the hydrogel portion and the liquid polymer interface. The collagen sponge in the porous periphery was removed by digestion using bacterial collagenase (Collagenase Type 2, Worthington Biochemical Corporation) for 16 hours to create the interconnected porous hydrogel structure in the hydrogel periphery portion of the implant.

After collagenase digestion, the completed implants were washed at least 5 times (10 minutes each) on a rocker with deionized water and then placed in 100% ethyl alcohol for at least 1 hour in order to dehydrate the hydrogel portion. The implants were then removed from the alcohol solution and allowed to air dry for at least 4 hours at room temperature under laminar air flow.

Example 4—Changes in Hydrogel Size after Dehydration

Hydrogels prepared as set forth in Example 1 were dehydrated as set forth in Example 3. The total hydrogel, the solid hydrogel (core) and the porous periphery or edge was measured both in diameter and in thickness. The change in hydrogel diameter after dehydration showed about a 44% decrease in diameter at the top surface and about a 31% decrease in diameter at the bottom surface from the initial size of the hydrogel (FIG. 3A). There was a smaller change in the height of the hydrogel with about a 22% decrease in thickness from the pre-dehydrated thickness (FIG. 3B).

Example 5—Rehydration Times of Solid Hydrogel and Porous Periphery of the Hydrogel Implants made according to Example 1 and dehydrated as in Example 3 were rehydrated by soaking the implants in phosphate buffered saline solution at room temperature. The diameter and the thickness of the entire hydrogel and the solid hydrogel (core) were measured initially, after dehydration, 15 minutes, 1 hour, 2 hours, 6 hours, and 4 days post rehydration. As shown in FIG. 4A, the solid hydrogel (core) and porous hydrogel periphery of the implants rehydrated at different rates with the solid hydrogel rehydrating in about 2 hours and the porous hydrogel periphery fully rehydrating in about 1 hour. Little difference is seen in the thickness of the hydrogel during rehydration (FIG. 4B).

Example 6—Implantation of the Implant

The implant manufactured using Examples 1-3 was implanted into the trochlear groove of a horse, using the following method:

The alignment tool 200 shown in FIG. 13A was used to place a Kirschner wire 201 (K-wire) perpendicular to the surface of the cartilage surrounding the defect (see FIG. 13C). The surface of the alignment tool was curved to match the surface curvature of the cartilage. The alignment tool was cannulated to allow the K-wire to pass through the guide and be driven perpendicular to the surface of the cartilage (see FIG. 13B). The tool 200 thus contains a central cannula (lumen) 210 formed therein. CT scans were used to determine the surface topography of the trochlear groove of the horse and matched the surface of the tool to the curvature of the cartilage in the groove.

Figure 15A:
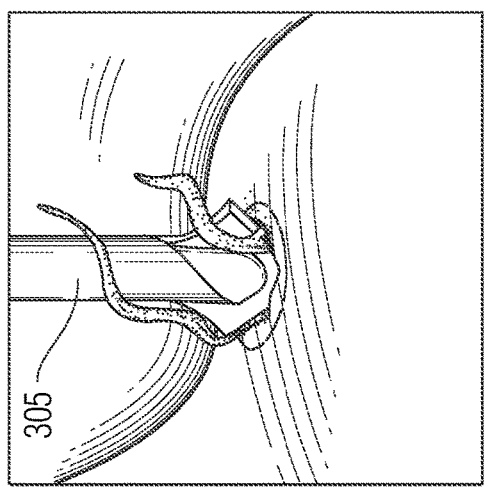
FIGS. 15A, 15B, 15C, and 15D show representative views of drilling the defect in an arthroscopic horse implantation.
Figure 15B:
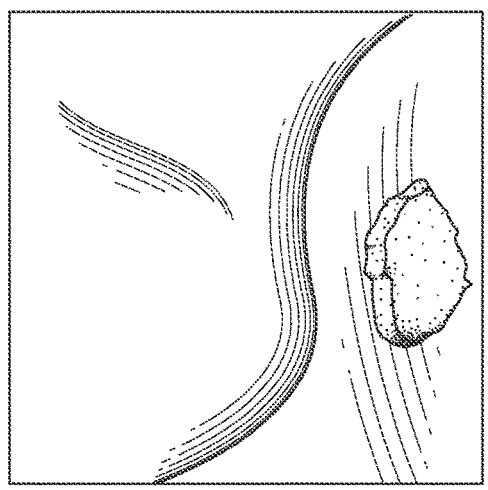
Figure 15C:
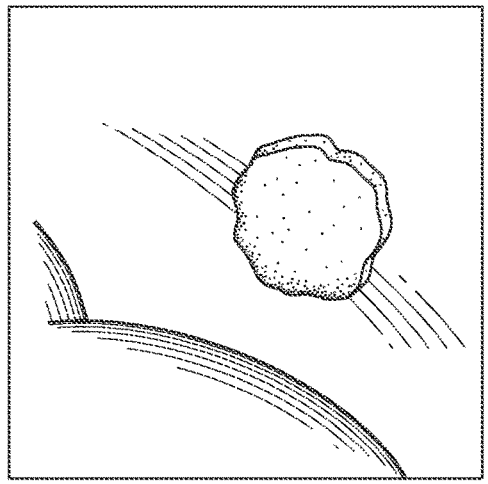
Figure 15D:
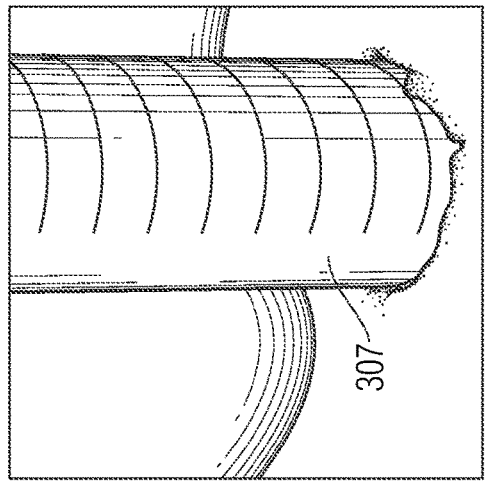

A cartilage scoring tool 300 (FIG. 14A) was used to score edges of defect. The cartilage scoring tool was cannulated to maintain perpendicular alignment with the cartilage surface by fitting concentrically over the k-wire. The cartilage scoring tool 300 was used to score the edges of the cartilage to create clean edges around the defect (FIGS. 14B and C). Also by scoring the cartilage to the bone surface, the thickness of the cartilage was effectively measured and the appropriate thickness of the hydrogel region of the implant that should be used in the patient was determined. A 9 mm diameter half-moon reamer 305 (Arthrex, Catalogue #: 031247) was placed over the K-wire and drilled to the desired depth (FIG. 15A). FIG. 15A shows an arcuate line that depicts the previous scored surface (see discussion above with respect to FIGS. 14A-C). For the large animal study done in this example, the depth was maintained at approximately 10 mm from the surface of the cartilage. The K-wire was removed and the defect was cleared of any debris (FIGS. 15B and C). A 9 mm diameter measuring instrument 307 was used to measure the final depth of the defect (FIG. 15D).

Based on the depth of the defect, an implant with the same height as the defect depth was chosen. A delivery tube 400 (see FIGS. 16C-D) was placed over the defect, and visually aligned using the cutout windows 410 at the distal tip. The implant 100 was then inserted into the end of the delivery tube 400 and an insertion rod 420 was then used to insert the implant 100 into the defect until the hydrogel surface 110, 120 was flush with the cartilage surface (FIG. 16E).

Figures 8A, 8B:
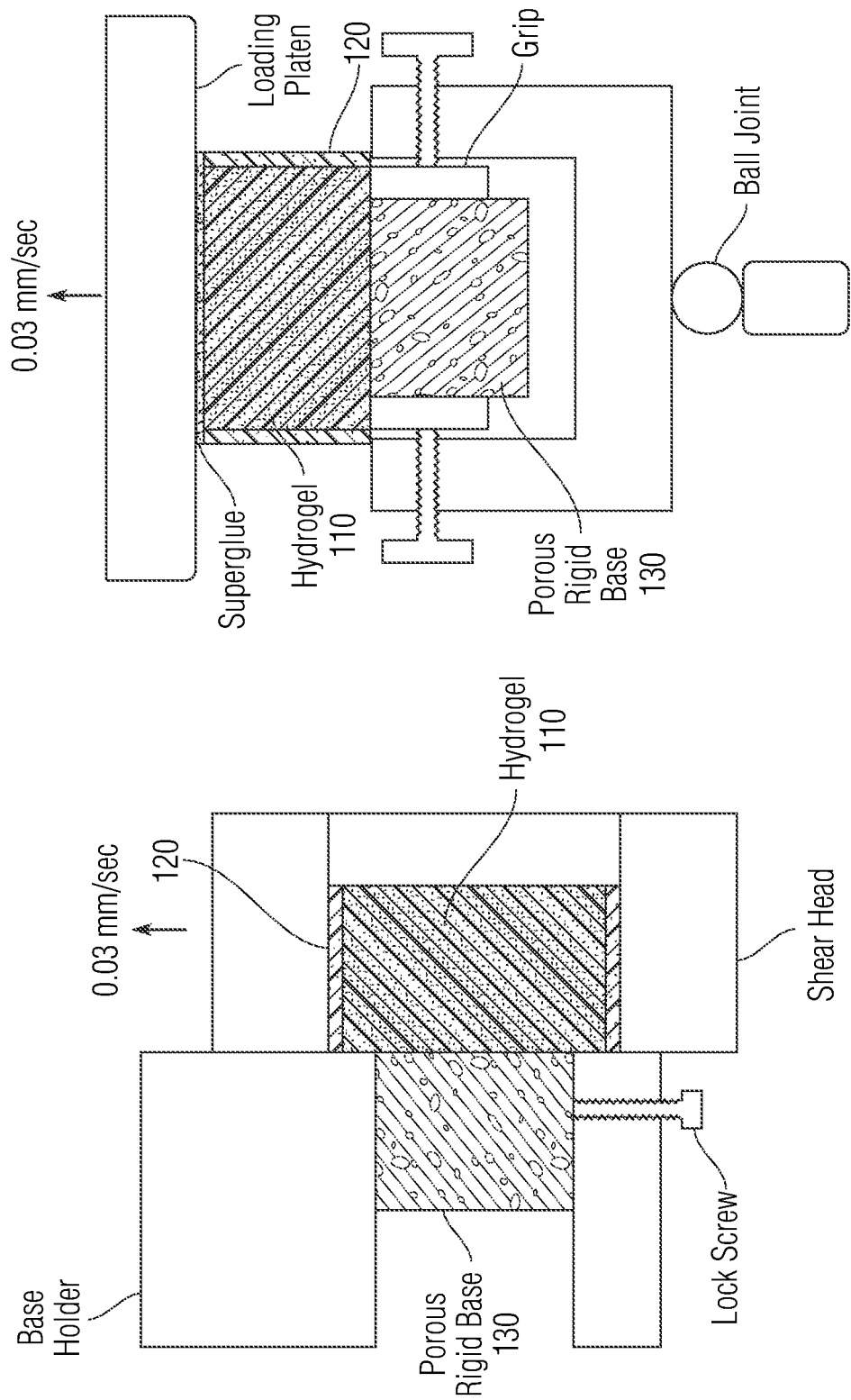
FIG. 8A is a schematic of a test to determine the ultimate interfacial shear stress between the porous rigid base and the hydrogel.
FIG. 8B is a schematic of a test to determine the ultimate interfacial tensile stress between the porous rigid base and the hydrogel.

Example 7—The Integration Between the Hydrogel and Porous Rigid Base Resist Forces The integration between the hydrogel and the porous rigid base of the preferred implant design for osteochondral defects manufactured as set forth in Examples 1-3 was tested in both shear and tension. For testing the integration in shear, the porous rigid base and hydrogel were fixed as shown in FIG. 8A. The shear head was moved at a rate of 0.03 mm/sec to induce shear at the interface of the porous rigid base and the hydrogel. Using this method, the ultimate shear stress at the hydrogel and porous rigid base was determined to be 0.4 MPa.

To determine the integration strength of the implant in tension, the implant was fixed as shown in FIG. 8B. The loading platen was displaced at a rate of 0.03 mm/sec and the tensile stress required to separate the hydrogel and porous rigid base was found to be 0.22 MPa.

The implant withstood forces that would be expected for use in treatment, repair and replacement of osteochondral defects.

Example 8—Implants can Restore Normal Mechanical Function

The implants made according to Examples 1-3 were tested in human cadaver knees. The implant was inserted using the instrumentation designed and using the technique for implantation described in Example 6. The implants were placed in the defect flush to about 0.5 mm proud to the surface of the adjacent articular cartilage in the cadaveric knees.

Electronic stress sensors (Tekscan, Inc, South Boston Mass.) were placed under the meniscus of the cadaveric knees on top of the tibial plateau to measure the stress on the surface of the tibial cartilage. The cadaveric knee joints were placed on a Stanmore Knee simulator and subjected to simulate level walking while intact and with a created defect. The defect was then filled with completed implants as described in Examples 1-3 containing solid PVA cores with elastic modulus ranging between 50 kPa to 500 kPa and 0.5 mm proud from the surface of the cartilage. Using this embodiment of the implant manufactured to treat, repair or replace osteochondral defects, the contact stress on the cartilage surface showed that the devices were able to restore normal joint loading within 10% of the intact condition having an elastic modulus of 100 kPa. See FIG. 12.

REFERENCES

1. Bekkers, J. E., et al. (2009). "Treatment selection in articular cartilage lesions of the knee: a systematic review." *Am J Sports Med* 37 Suppl 1: 148S-155S.
2. Buckwalter, J. A. and H. J. Mankin (1998). "Articular cartilage: tissue design and chondrocyte-matrix interactions." *Instr Course Lect* 47: 477-486.
3. Choi, K., et al. (1990) "The elastic moduli of human subchondral, trabecular, and cortical bone tissue and the size-dependency of cortical bone modulus." *J Biomech* 23(11):1103-13.
4. Cole, B. J. and S. J. Lee (2003). "Complex knee reconstruction: articular cartilage treatment options." *Arthroscopy* 19 Suppl 1: 1-10.
5. Deneweth, J. M., et al. (2013) "Heterogeneity of tibial plateau cartilage in response to a physiological compressive strain rate." *J Orthop Res* 31(3):370-5.
6. Magnussen, R. A., et al. (2008). "Treatment of focal articular cartilage defects in the knee: a systematic review." *Clin Orthop Relat Res* 466(4): 952-962.
7. Mauck, R. L., et al. (2002). "Influence of seeding density and dynamic deformational loading on the developing structure/function relationships of chondrocyte-seeded agarose hydrogels." *Ann Biomed Eng* 30(8): 1046-1056.
8. Ng, K. W., et al. (2012) "A novel macroporous polyvinyl alcohol scaffold promotes chondrocyte migration and interface formation in an in vitro cartilage defect model." *Tissue Eng Part A* 18(11-12): 1273-81.
9. Radin, E. L., et al. (1970) "A comparison of the dynamic force transmitting properties of subchondral bone and articular cartilage." *J Bone Joint Surg Am* 52(3):444-56.
10. Shelbourne, K. D., et al. (2003). "Outcome of untreated traumatic articular cartilage defects of the knee: a natural history study." *J Bone Joint Surg Am* 85-A Suppl 2: 8-16.

The invention claimed is:

1. A method of manufacturing an implant suitable for implantation into a mammal for the treatment, repair or replacement of defects or injury in musculoskeletal tissue, comprising:
   a. creating geometric features in a surface of a porous rigid base, wherein the porous rigid base contain micropores;
   b. adding a liquid polymer to the geometric features and the surface of the porous rigid base, such that the geometric features are filled and the surface covered, to create a porous rigid base-polymer construct;
   c. placing a hydrogel on the porous rigid base-polymer construct to create the implant, wherein the hydrogel comprises a solid hydrogel in the center and a porous hydrogel at the periphery or edge of the hydrogel; and
   d. freezing and thawing the implant;
      wherein the freeze/thaw process is performed 1 to 5 times and wherein the resulting implant comprises the solid hydrogel, the porous hydrogel adjacent to the solid hydrogel and the porous rigid base attached only to the solid hydrogel.

2. The method of claim 1, wherein the freezing of the implant is performed at about −20° C. for about 4 to 24 hours and the subsequent thawing of the implant is performed at about 25° C. for about 4 to 12 hours.

3. The method of claim 1, wherein the geometric features are chosen from the group consisting of holes, macropores, and steps.

4. The method of claim 1, wherein the hydrogel comprises at least one solid hydrogel portion and at least one porous hydrogel portion.

5. A method of manufacturing an implant suitable for implantation into a mammal for the treatment, repair or replacement of defects or injury in musculoskeletal tissue, comprising:
   a. creating geometric features in a surface of a porous rigid base, wherein the porous rigid base contain micropores;
   b. adding a liquid polymer to the geometric features and the surface of the porous rigid base, such that the geometric features are filled and the surface covered, to create a porous rigid base-polymer construct;
   c. placing a hydrogel on the porous rigid base-polymer construct to create the implant; and
   d. freezing and thawing the implant;
   e. wherein the freeze/thaw process is performed 1 to 5 times,
   wherein the hydrogel is manufactured comprising the steps:
   a. soaking a degradable polymer sponge in deionized water for a period of about 1 hour to 5 days;
   b. centrifuging the sponge during the soaking;
   c. substituting the water with a non-biodegradable polymer in steps of increasing concentration up to a desired final concentration;
   d. freezing the sponge to about −20° C. for about 4 to 24 hours and subsequently thawing the sponge at about 25° C. for about 4 to 12 hours, wherein the freeze/thaw process is performed 1 to 8 times;
   e. removing a center section from the sponge after performing steps a.-d;
   f. adding additional non-biodegradable polymer to the section; and
   g. performing additional freeze/thaw processes to create a hydrogel with a solid hydrogel in the center and a porous hydrogel at the periphery or edge of the hydrogel.

6. A method of manufacturing an implant suitable for implantation into a mammal for the treatment, repair or replacement of defects or injury in musculoskeletal tissue, comprising:
   a. creating geometric features in a surface of a porous rigid base, wherein the porous rigid base contain micropores;
   b. adding a liquid polymer to the geometric features and the surface of the porous rigid base, such that the geometric features are filled and the surface covered, to create a porous rigid base-polymer construct;
   c. placing a hydrogel on the porous rigid base-polymer construct to create the implant; and
   d. freezing and thawing the implant;
   e. wherein the freeze/thaw process is performed 1 to 5 times,
   wherein the hydrogel is manufactured comprising the steps of:
   a. soaking a degradable polymer sponge in deionized water for a period of about 1 hour to 5 days;
   b. centrifuging the sponge during the soaking;
   c. substituting the water with a non-biodegradable polymer in steps of increasing concentration up to a desired final concentration;

d. freezing the sponge to about −20° C. for about 4 to 24 hours and subsequently thawing the sponge at about 25° C. for about 4 to 12 hours, wherein the freeze/thaw process is performed 1 to 8 times;

e. cutting the sponge into sections after performing steps a.-d;

f. adding additional non-biodegradable polymer to some of the sections from step e.;

g. performing additional freeze/thaw processes in the sections from step f. to create hydrogel sections comprising a solid hydrogel;

h. layering alternating porous hydrogel sections made from steps a.-d. and solid hydrogel sections made from steps a.-g.; and i. performing additional freeze/thaw cycles to connect the sections, to create a hydrogel with alternating porous hydrogel sections and solid hydrogel sections.

7. The method of claim 1, further comprising the step of digesting away degradable polymer in the implant.

8. The method of claim 1, comprising the additional step of dehydrating the implant prior to implantation, such that the solid hydrogel and the porous hydrogel decrease in size and/or change shape, and upon implantation, the implant rehydrates and the solid hydrogel and the porous hydrogel increase in size and/or regain their shapes, and, wherein the porous hydrogel rehydrates prior to the solid hydrogel.

9. The method of claim 1, wherein the geometric feature is a central macropore.

10. The method of claim 1, wherein the porous rigid base is comprised of metal.

11. The method of claim 1, wherein the geometric features in a surface of the porous rigid base are formed by methods consisting of physical treating the porous rigid base.

\* \* \* \* \*